(12) United States Patent
Adie et al.

(10) Patent No.: US 12,703,878 B2
(45) Date of Patent: Aug. 11, 2026

(54) CLOSED LINEAR DNA PRODUCTION

(71) Applicant: Touchlight IP Limited, Hampton (GB)

(72) Inventors: Thomas Adie, Hampton (GB); Neil Porter, Hampton (GB); Paul Rothwell, Hampton (GB)

(73) Assignee: Touchlight IP Limited, Hampton (GB)

( * ) Notice: Subject to any disclaimer, the term of this patent is extended or adjusted under 35 U.S.C. 154(b) by 307 days.

(21) Appl. No.: 17/938,553

(22) Filed: Oct. 6, 2022

(65) Prior Publication Data

US 2023/0272461 A1 Aug. 31, 2023

Related U.S. Application Data

(63) Continuation of application No. 16/325,621, filed as application No. PCT/GB2017/052413 on Aug. 16, 2017, now Pat. No. 11,505,821.

(30) Foreign Application Priority Data

Aug. 16, 2016 (GB) ..................................... 1613994
Dec. 22, 2016 (GB) ..................................... 1621954

(51) Int. Cl.
*C12P 19/34* (2006.01)
*C12Q 1/6844* (2018.01)

(52) U.S. Cl.
CPC ...... *C12Q 1/6844* (2013.01); *C12Q 2521/113* (2013.01); *C12Q 2525/151* (2013.01);
(Continued)

(58) Field of Classification Search
USPC ............ 435/6.1, 6.11, 6.12, 91.1, 91.2, 183; 436/94, 501; 536/23.1, 24.3, 24.33, 25.3
See application file for complete search history.

(56) References Cited

U.S. PATENT DOCUMENTS 9,012,620 B2 4/2015 Schroff et al.
2004/0110282 A1 6/2004 Kanda et al.
(Continued)

FOREIGN PATENT DOCUMENTS

CA 2651568 A1 11/2007
CN 101313067 A 11/2008
(Continued)

OTHER PUBLICATIONS

International Search Report for PCT/GB2017/052413, dated Nov. 7, 2017 (2 pages).
(Continued)

*Primary Examiner* — Frank W Lu
(74) *Attorney, Agent, or Firm* — Bookoff McAndrews, PLLC

(57) ABSTRACT

The present invention relates to improved processes for production of closed linear deoxyribonucleic acid (DNA), in particular cell-free enzymatic production of closed linear DNA molecules, preferable using a closed linear DNA as a template for DNA synthesis. The invention further relates to a novel closed linear DNA species, suitable for use as a template in the improved processes for production of closed linear DNA. Further, the invention pertains to the intermediate products of the processes, since this enables the production of larger quantities of closed linear DNA from the template than with methods known in the art.

8 Claims, 15 Drawing Sheets

Specification includes a Sequence Listing.

(52) U.S. Cl.
CPC . *C12Q 2525/301* (2013.01); *C12Q 2525/307* (2013.01); *C12Q 2531/119* (2013.01); *C12Q 2531/125* (2013.01)

(56) References Cited

U.S. PATENT DOCUMENTS

| | | | | |
|---|---|---|---|---|
| 2012/0282283 | A1* | 11/2012 | Hill ...................... | C12Q 1/6844 435/194 |
| 2013/0203123 | A1 | 8/2013 | Nelson et al. | |
| 2013/0216562 | A1 | 8/2013 | Porter et al. | |

FOREIGN PATENT DOCUMENTS

| | | | |
|---|---|---|---|
| EP | 2 692 870 | A1 | 2/2014 |
| WO | WO 2009/120372 | A2 | 10/2009 |
| WO | WO 2010/086626 | A1 | 8/2010 |
| WO | WO 2012/017210 | A1 | 2/2012 |
| WO | WO 2016/034849 | A1 | 3/2016 |

OTHER PUBLICATIONS

Mei, L. et al., “Self-assembled multifunctional DNA nanoflowers for the circumvention of multidrug resistance in targeted anticancer drug delivery,” *Nano Research*, vol. 8, pp. 3447-3460 and Supplementary Material (2015).
Lv, Y. et al., “Preparation and biomedical applications of programmable and multifunctional DNA nanoflowers,” *Nature Protocols*, vol. 10, pp. 1508-1524 (2015).
Zhu, G. et al., “Noncanonical Self-Assembly of Multifunctional DNA Nanoflowers for Biomedical Applications,” *Journal of the American Chemical Society*, vol. 135, pp. 16438-16445 and Supplemental Information (2013).
“TelN Protelomerase,” New England Biolab, <URL: https://.neb.com/products/m0651-teln-protelomerase#Product%20Information>, printed on Sep. 10, 2021.
Jiang, X. et al., “Advanced Design of Dumbbell-shaped Genetic Minimal Vectors Improves Non-coding and Coding RNA Expression”, Molecular Therapy, 2016, vol. 24, Issue No. 9, pp. 1581-1591.

* cited by examiner

```
Organism  45   40   35   30   25   20   15   10   5   1   1   5   10   15   20   25   30   35   40   45

A.   5' TAT C AGCA C ACAA T TGCC C ATTATACGC GCGTATAAT G GACT A TTGT G TGCT G ATA 3'
     3' ATA G TCGT G TGTT A ACGG G TAATATGCG CGCATATTA C CTGA T AACA C ACGA C TAT 5'

B.   5' C AGCA C ACAA C AGCC C ATTATACGC GCGTATAAT G GGCT A TTAT G TGCT G 3'
     3' G TCGT G TGTT G TCGG G TAATATGCG CGCATATTA C CCGA T AATA C ACGA C 5'

C.   5' T A GTCA C CTAT T TCAG C ATACTACGC GCGTAGTAT G CTGA A ATAG G TTAC T G 3'
     3' A T CAGT G GATA A AGTC G TATGATGCG CGCATCATA C GACT T TATC C AATG A C 5'

D.   5' C CTAT A TTGG G CCAC C TATG T ATGC A CAGT T CGCC C ATACTATAC GTATAGTAT G GGCG A ACTG T GCAT A CATA G GTGG C CCAA T ATAG G 3'
     3' G GATA T AACC C GGTG G ATAC A TACG T GTCA A GCGG G TATGATATG CATATCATA C CCGC T TGAC A CGTA T GTAT C CACC G GGTT A TATC C 5'

E.   5' G GGAT C CCGT T CCAT A CATA C ATGT A TCCA T GTGG C ATACTATAC GTATAGTAT G CCGA T GTTA C ATAT G GTAT C ATTC G GGAT C CCGT T 3'
     3' C CCTA G GGCA A GGTA T GTAT G TACA T AGGT A CACC G TATGATATG CATATCATA C GGCT A CAAT G TACA C CATA G TAAG C CCTA G GGCA A 5'

F.   5' TACT A AATA A ATATTATAT ATATAATTT T TTAT T AGTA 3'
     3' ATGA T TTAT T TATAATATA TATATTAAA A AATA A TCAT 5'

G.   5' TAAC T GTAC A TATA C CAAC C TGCA C AGGT G TACA T ATAGTCTAA TTAGACTAT A TGTA C ACCT G TGCA G GTTG G TATA T GTAC A GTTA 3'
     3' ATTG A CATG T ATAT G GTTG G ACGT G TCCA C ATGT A TATCAGATT AATCTGATA T ACAT G TGGA C ACGT C CAAC C ATAT A CATG T CAAT 5'

H.   5' G CGAT C GATC A TAAT A ACAATATCA TGATATTGT T ATTG T AATC G ATCG C 3'
     3' C GCTA G CTAG T ATTA T TGTTATAGT ACTATAACA A TAAC A TTAG C TAGC G 5'
```

Fig. 4

| Stem loop sequence | AAATATAAACCTAAAGTCTCCCTACAAGTAAGTTTATATTT |
|---|---|
| 4to11 primer | GAGGGAT |
| 3to12 primer | AGAGGGATG |
| 2to13 primer | CAGAGGGATGT |
| 1to14 primer | TCAGAGGGATGTT |
| 0to 15 primer | TTCAGAGGGATGTTC |

Fig. 10A

| Lane | Sample |
|---|---|
| 1 | 1kb ladder (NEB) |
| 2 | TelN digest from 4to11 primed RCA |
| 3 | TelN digest from 3to12 primed RCA |
| 4 | TelN digest from 2to13 primed RCA |
| 5 | TelN digest from 1to14 primed RCA |
| 6 | TelN digest from 0to15 primed RCA |

Fig. 10B

CLOSED LINEAR DNA PRODUCTION

CROSS-REFERENCE TO RELATED APPLICATIONS

This application is a continuation of U.S. application Ser. No. 16/325,621, filed on Feb. 14, 2019, now U.S. Pat. No. 11,505,821, which is the U.S. national stage entry under 35 U.S.C. § 371 of International Application No. PCT/GB2017/052413, filed on Aug. 16, 2017, incorporated by reference herein, PCT/GB2017/052413 claiming the benefit of priority to GB Application No. 1613994.1, filed on Aug. 16, 2016, and GB Application No. 1621954.5, filed on Dec. 22, 2016.

SEQUENCE LISTING

This application contains a sequence listing, submitted electronically in XML format under the filename 00012-0038-01000.xml, which is incorporated by reference herein in its entirety. The XML copy of the sequence listing was created on May 16, 2023, and is 68,292 bytes in size.

FIELD

The present invention relates to improved processes for production of closed linear deoxyribonucleic acid (DNA), in particular cell-free enzymatic production of closed linear DNA molecules, preferably using a closed linear DNA as a template for DNA synthesis. The invention further relates to a novel closed linear DNA species, suitable for use as a template in the improved processes for production of closed linear DNA. Further, the invention pertains to the intermediate products of the processes, since this enables the production of larger quantities of closed linear DNA from the template than with methods known in the art.

BACKGROUND

The cell-free production of closed linear DNA has previously been described by the applicant in WO2010/086626 and WO2012/017210; which are hereby incorporated by reference. The method described in these applications relates to the production of linear double stranded DNA covalently closed at each end (closed linear DNA) using a DNA template, wherein the DNA template comprises at least one protelomerase recognition sequence, and where the template is amplified using at least one DNA polymerase and processed using a protelomerase enzyme to yield closed linear DNA. The closed ends of the closed linear DNA each include a portion of a protelomerase recognition sequence. The use of a closed linear DNA as a template is envisioned in the listed applications, and the use of such a template is advantageous, since it means that the minimum amount of reagents are wasted during production. Small-scale experimental production of closed linear DNA works well with a closed linear DNA template using these methods. However, the yield is lower than expected, and not sufficient for preparation of commercially viable amounts of closed linear DNA.

When a closed linear DNA template is used in the methods described above, the closed linear DNA molecule may be viewed as a single stranded circular molecule as depicted in FIG. 5. Usually, closed linear DNA as described herein is essentially fully complementary in sequence, although some minor variations or "wobbles" may be tolerated by the structure. Thus, the closed linear DNA may be at least 95% complementary, or at least 96, 97, 98, 99 or 100% complementary in sequence. When denatured, it is effectively a circular molecule comprising both forward (sense or plus) and reverse (antisense or minus) strands adjacent to each other. This is in contrast to plasmid DNA where the complementary sequences (minus and plus) lie on separate circular strands (FIG. 5, A compared to B).

The unique structure of closed linear DNA means that it can renature more readily than a plasmid and therefore oligonucleotide priming for DNA amplification by DNA polymerase can present more of a challenge. This is particularly the case where single primers are used that bind to the palindromic sequences comprising the protelomerase recognition sequence within the hairpin. The closed linear DNA template may be amplified using a strand-displacing polymerase which initially produces concatamers comprising single strands of DNA, each concatamer comprising multiple repeat units of the DNA template, each repeat unit being complementary in sequence to the original sequence of the closed linear DNA template. However, since each template includes both the plus and minus strands, the concatameric single strand DNA produced includes alternate minus and plus strand sequences as a "repeat unit". This can be compared with amplification from a plasmid, where the single strand that is produced from the circular template (either strand) comprises multiple repeats of the same sequence in the opposite orientation (i.e. a sense strand is replicated as a concatamer comprising multiple repeat units of the antisense strand). Thus, there are distinct structural differences in the concatameric product produced as a result of strand displacement replications of a plasmid DNA template and a closed linear DNA template. It is these structural differences in the product of amplification from a closed linear DNA that may result in inefficient generation of closed linear DNA.

Since the concatamers that are initially produced from the amplification of a closed linear DNA are a single strand of DNA, they are theoretically available as a template for further primer binding and thus further replication. This step generates a concatamer with two distinct complementary strands, and then either stand may be displaced to replicate a further new strand. The "double stranded" concatamer thus comprises two distinct complementary strands of DNA. Notionally, large amounts of amplification can take place from a small amount of initial template, due to the nature of the strand-displacement polymerase used. The double stranded DNA concatamer is important, since this is ultimately the substrate for the protelomerase enzyme used in the process of manufacture of closed linear DNA, as described in previous applications, such as WO2010/086626 and WO2012/017210.

However, the inventors have established that when closed linear DNA is used as a template, some or most of the "product" is formed as DNA nanoflowers, despite the addition of a protelomerase enzyme to cleave the complete protelomerase recognition sequences in the double stranded concatamers and form closed linear DNA. This is shown on FIG. 6. The single strand of DNA comprising alternate "plus" and "minus" strands is effectively self-complementary and therefore readily folds internally to compact structures known as DNA nanoflowers. These are essentially long single strands of concatameric DNA which have self-hybridised and are no longer available for priming or processing with protelomerase, since the strands are packed tightly together. This is far from the ideal scenario. Required for standard methods of closed linear DNA production is the production of linear double stranded concatamers using the initial single strand concatameric DNA as a template, and this double stranded intermediate is processable by a protelomerase to form closed linear DNA molecules (step K of FIG. 5). The complete protelomerase recognition sequence is formed from two complementary strands of DNA, in a duplex formation.

The adjacent plus—minus nature of the initial single strand of DNA produced by a strand-displacing polymerase acting on a closed linear DNA template results in extensive internal hybridisation of the concatamers to produce DNA nanoflowers (FIG. 6, step F). This compact, folded DNA structure prevents efficient oligonucleotide primer binding (FIG. 6, step G) necessary to convert the DNA nanoflowers into protelomerase-processable linear double stranded concatamers as used in the methods current in the art.

There is therefore a need for an improved in vitro process to efficiently amplify a closed linear DNA template at high DNA yields or alternatively put, to decrease the production of impenetrable DNA nanoflowers during production of closed linear DNA, and/or to increase the conversion of already formed DNA nanoflowers into closed linear DNA

Summary

The present invention relates to a process for the in vitro, cell free production of closed linear DNA from a closed linear DNA template. The process may allow for enhanced production of closed linear DNA compared to current methodologies. This significantly increases productivity whilst reducing the cost of producing closed linear DNA, particularly on a larger scale.

Accordingly there is provided a cell-free method of producing closed linear DNA molecules comprising:

(a) contacting a template comprising linear, double stranded DNA molecule covalently closed at each end by a portion of a protelomerase recognition sequence and comprising at least one stem loop motif with a strand-displacing polymerase under conditions promoting amplification of said template in the presence of at least one primer which is capable of binding specifically to a primer binding site within said stem loop motif;

(b) contacting the DNA produced in (a) with at least one protelomerase under conditions promoting production of closed linear DNA.

Optionally, the template may comprise further protelomerase recognition sequences, in addition to those portions of protelomerase recognition sequence located at the closed ends or caps of the closed linear DNA template. If the template comprises one or more additional or further protelomerase recognition sequences, the additional protelomerase recognition sequences may be positioned at any site in the double stranded section of the template. Preferably, these additional or further protelomerase recognition sequences are distinct to and separate from the at least one stem loop motif. The additional protelomerase recognition sequence(s) may be separated from one or both of the closed ends of the closed linear DNA by the at least one stem loop motif.

Optionally, each of the protelomerase recognition sequences or portions thereof may be the same sequence or different sequences, each independently of the other. Different recognition sequences will be acted upon by different protelomerase enzymes, and therefore the appropriate protelomerase enzymes will be required for the production of closed linear DNA.

According to a second aspect, the present invention relates to a linear, double stranded DNA molecule covalently closed at each end by a portion of a protelomerase recognition sequence, wherein the sequence of said linear, double stranded DNA molecule includes at least one stem loop motif.

According to a third aspect, the present invention relates to a concatameric DNA molecule comprising a single strand of DNA, said single strand comprising two or more identical units of DNA sequence covalently linked together in a series, each unit comprising at least one portion of a protelomerase recognition sequence and at least one stem loop structure or motif. Optionally, the concatamer is in vitro and cell-free. Optionally, the unit comprises at least one further protelomerase recognition sequence.

According to the third aspect, there may be provided concatameric DNA molecule comprising a single strand of DNA, said single strand comprising two or more identical units of DNA sequence covalently linked together in a series, each unit comprising at least one stem loop structure or motif flanked on either side by at least one portion of a protelomerase recognition sequence. Optionally, said portions are recognised by the same or different protelomerase enzymes.

According to the third aspect, the stem loop structure may comprise all or part of the sequence for a stem loop motif as hereinbefore described.

Further according to the third aspect, the units of DNA sequence are the sequence for a linear, double stranded DNA molecule as defined herein.

The single strand of concatameric DNA as described may form intra-strand base pairs, with the exception of the loop of the stem loop structure. Thus, the single strand of concatameric DNA may form a DNA nanoflower with open, single stranded loops. The invention thus extends to the single stranded concatamer as described herein, folded into a nanoflower.

According to a fourth aspect there is provided a kit, optionally suitable for performing the method of any aspect of the invention, said kit comprising:

(a) a linear, double stranded DNA molecule covalently closed at each end by a portion of a protelomerase recognition sequence, wherein the sequence of said linear, double stranded DNA molecule includes at least one stem loop motif;

(b) a protelomerase; and optionally;

(c) a bridging oligonucleotide.

The kit may further comprise a DNA polymerase and optionally a primer. Additionally, the kit may include any one or more of appropriate buffers, nucleotides, pyrophosphatase and/or nucleases.

According to any aspect of the invention the stem loop motif is a sequence, which may comprise two sequences flanking a central section. The stem loop motif is designed to form a stem loop structure under conditions suitable for the formation of secondary structure, such as when the sequence is present in a single strand of DNA, i.e. without a bound complementary but distinct second strand. Distinct strands have their own 3' and 5' termini. Optionally, said conditions are the amplification conditions used in the method of the present invention, and exemplary conditions are described further below.

According to any aspect or embodiments of the invention the central section of the motif is designed to be looped out as a single stranded DNA when the flanking sequences are brought together; either by self-complementary base pairs forming a stem or by use of a bridging oligonucleotide.

According to any aspect or embodiment of the invention, the stem loop motif or stem loop structure may comprise a primer binding site. This primer binding site is within the central section of the motif or structure, and thus within the single stranded section. Optionally, the primer binding site is surrounded by 1 or 2 adjacent single stranded sequences in the central section.

According to any aspect or embodiment of the invention, the stem loop motif or structure may comprise two flanking sequences to the central section, optionally designed to be self-complementary or designed to be complementary to a bridging oligonucleotide.

According to any aspect or embodiment of the invention, the stem loop motif or structure may be adjacent to or near to a portion of the protelomerase recognition sequence, wherein said portion is within the covalently closed end of the linear DNA molecule. Optionally, the sequence for the stem loop motif or structure is separated by up to 100 bases from the end of the portion of the protelomerase recognition sequence forming the closed end of the template molecule. Where additional protelomerase target sequences are present, these may be adjacent to the stem loop motifs or separate to them.

According to any aspect of the invention, there may be included two or more stem loop motifs in the DNA template, and thus two or more stem loop structures in the concatamer as defined previously. Each stem loop motif may be adjacent or near to a closed end of the closed linear DNA molecule.

According to any aspect of the invention, there may be included one or more additional protelomerase recognition sequences within the double stranded section of the template. Said additional protelomerase recognition sequences are distinct to those present at the closed ends of the template, and further are distinct to the one or more stem loop motifs.

Further embodiments are described below and in the claims. Further advantages are described below.

BRIEF DESCRIPTION OF THE DRAWINGS

The present invention will be described further below with reference to exemplary embodiments and the accompanying drawings, in which:

FIG. 4 shows the whole native recognition sequences for a selection of protelomerase enzymes, showing the sequences of both strands of the complementary DNA. Shown are the target sequences: the sequence of SEQ ID NO: 15 (*Escherichia coli* N15 TelN protelomerase), the sequence of SEQ ID NO: 16 (*Klebsiella* phage Phi K02 protelomerase), the sequence of SEQ ID NO: 17 (*Yersinia* phage PY54 protelomerase), the sequence of SEQ ID NO: 1 (*Halomonas* phage PhiHAP-1), the sequence of SEQ ID NO: 18 (*Vibrio* phage VP882 protelomerase), the sequence of SEQ ID NO: 19 (*Borrelia burgdorferi* protelomerase), the sequence of SEQ ID NO: 21 (*Vibrio parahaemolyticus* plasmid Vp58.5 protelomerase), and the sequence of SEQ ID NO: 20 (*Agrobacterium tumefaciens* TelA protelomerase). Where the minimum sequence length requirement for the cognate protelomerase is known, this has been indicated by shading the sequence grey, although the enzyme may accept some variation in sequence within this core recognition sequence. Nucleotides represented in bold and underlined indicate imperfections in the palindrome sequence. The vertical line through the sequences represents the centre of the perfect inverted sequence and the point at which the protelomerase cleaves and joins its specific recognition sequence;

Figure 8:
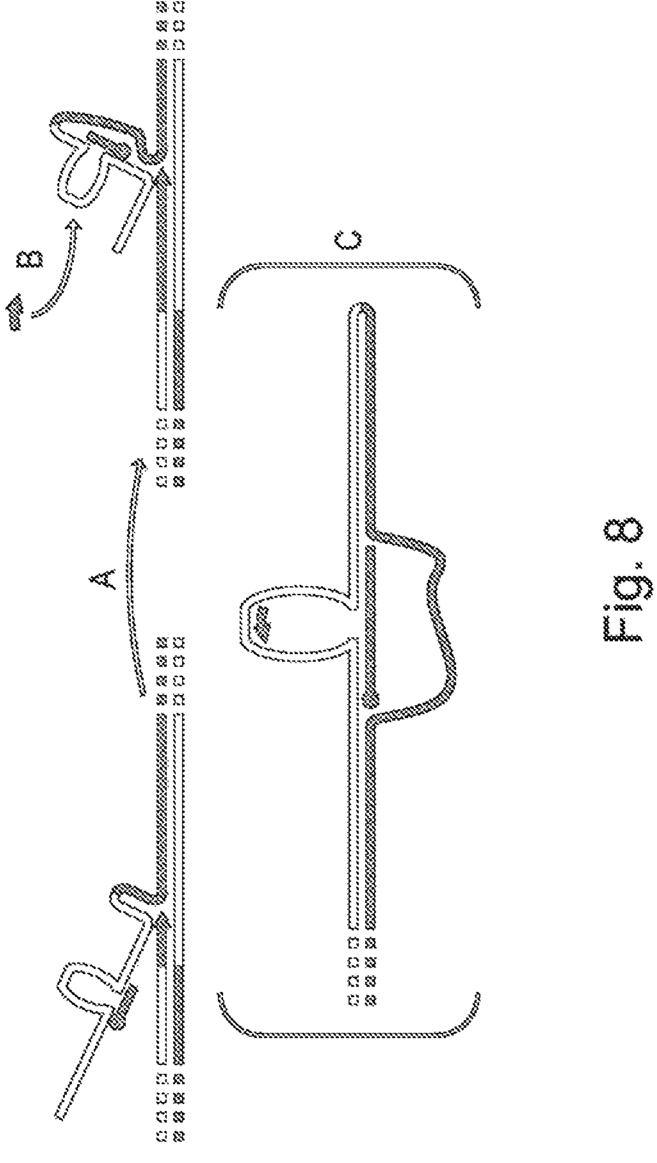

This allows the nanoflowers to have an "open loop" structure, in which a primer binding site is located. This enables the primer to anneal and the strand displacement polymerase to force open and convert the nanoflowers into linear double stranded concatameric DNA for processing into closed linear DNA. A depicts the introduction of primers to the template, B depicts the primers binding and amplification occurring, C shows the growth of the single stranded concatameric DNA, D and E show the replication of a single stranded concatamer of DNA, F shows the formation of DNA nanoflowers, except the stem loop motifs force the formation of single stranded regions in the nanoflower, enabling further primer binding (G). It should be noted that the embodiment shown involves the use of two primer species, but this method can equally be performed with one specific primer;

FIG. 8 depicts the use of a bridging oligonucleotide to hold the stem loop motif into an open loop structure. This is an alternative arrangement for the stem loop motif. The bridging oligonucleotide specifically binds to the flanking sequences of the stem loop motif, and forces out the central section into a loop of single stranded DNA. When such a structure is introduced during the process of the invention, it enables the central section of the stem loop motif to be single stranded, thus presenting the primer binding site for the primer to specifically anneal. A. The process of using a bridging oligonucleotide to create a loop within the stem loop motif. B. The binding of a primer to the primer binding site within the loop structure. C. The priming of the loop of the stem loop motif using a bridging oligonucleotide.

Figures 9A, 9B, 9C, 9D:
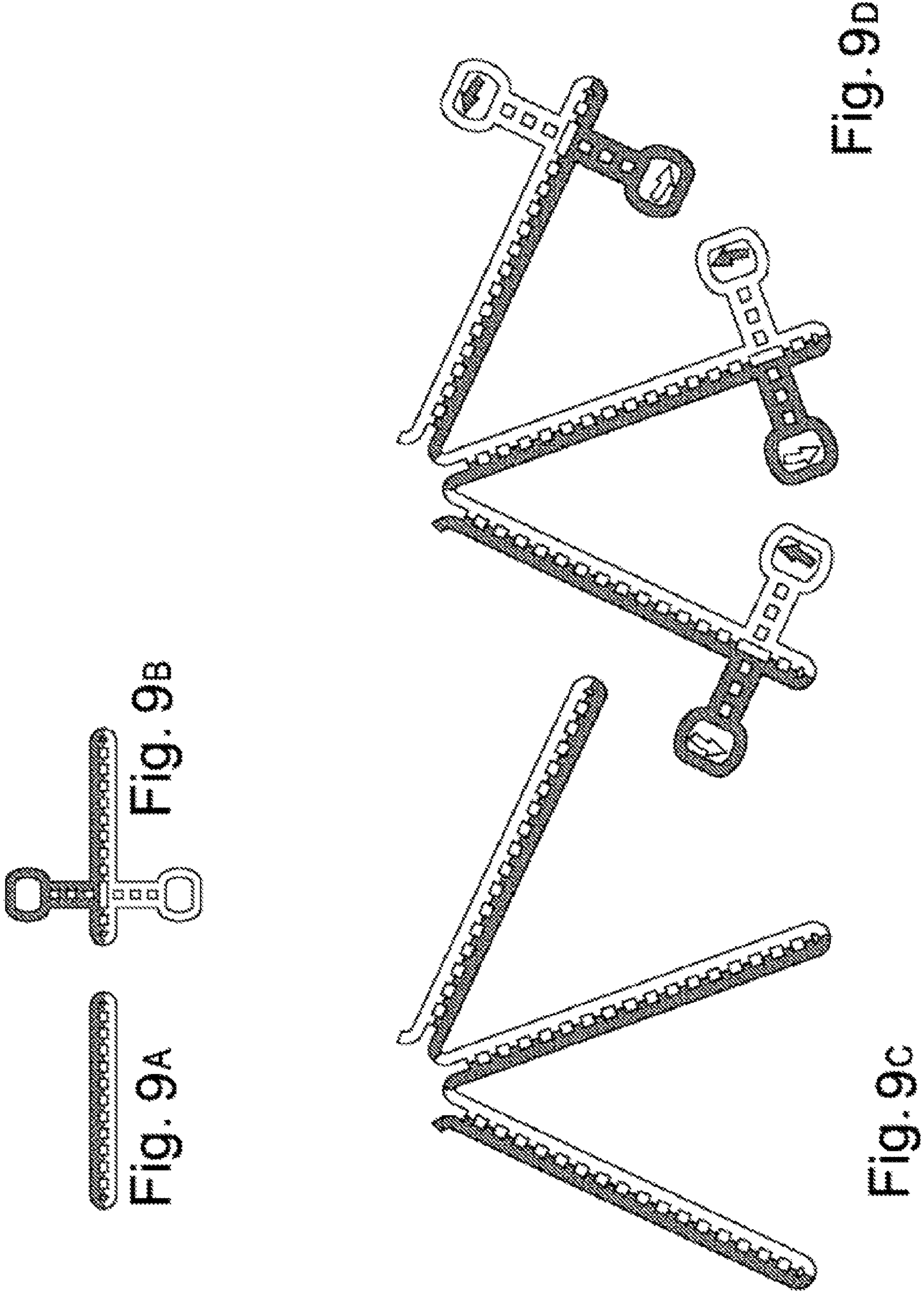

FIGS. 9A to 9D depict various structures discussed in this application depicted schematically. FIG. 9A is a closed linear DNA molecule with the ends of the molecule formed by a portion of a protelomerase target sequence. FIG. 9B is a closed linear DNA with a stem-loop motif as described in the present application. The stem loops are paired due to the complementary nature of the sequences present on the opposing sections of the DNA. FIG. 9C shows a DNA nanoflower, made from a single strand of DNA that has formed intra-strand base pairs between complementary sequences. FIG. 9D shows the same structure as 9C, with the addition of a stem loop motif to the sequence. This results in pairs of stem loops forming within the DNA nanoflower, permitting primer annealing and initiation of DNA synthesis in the direction shown.

Figure 11:
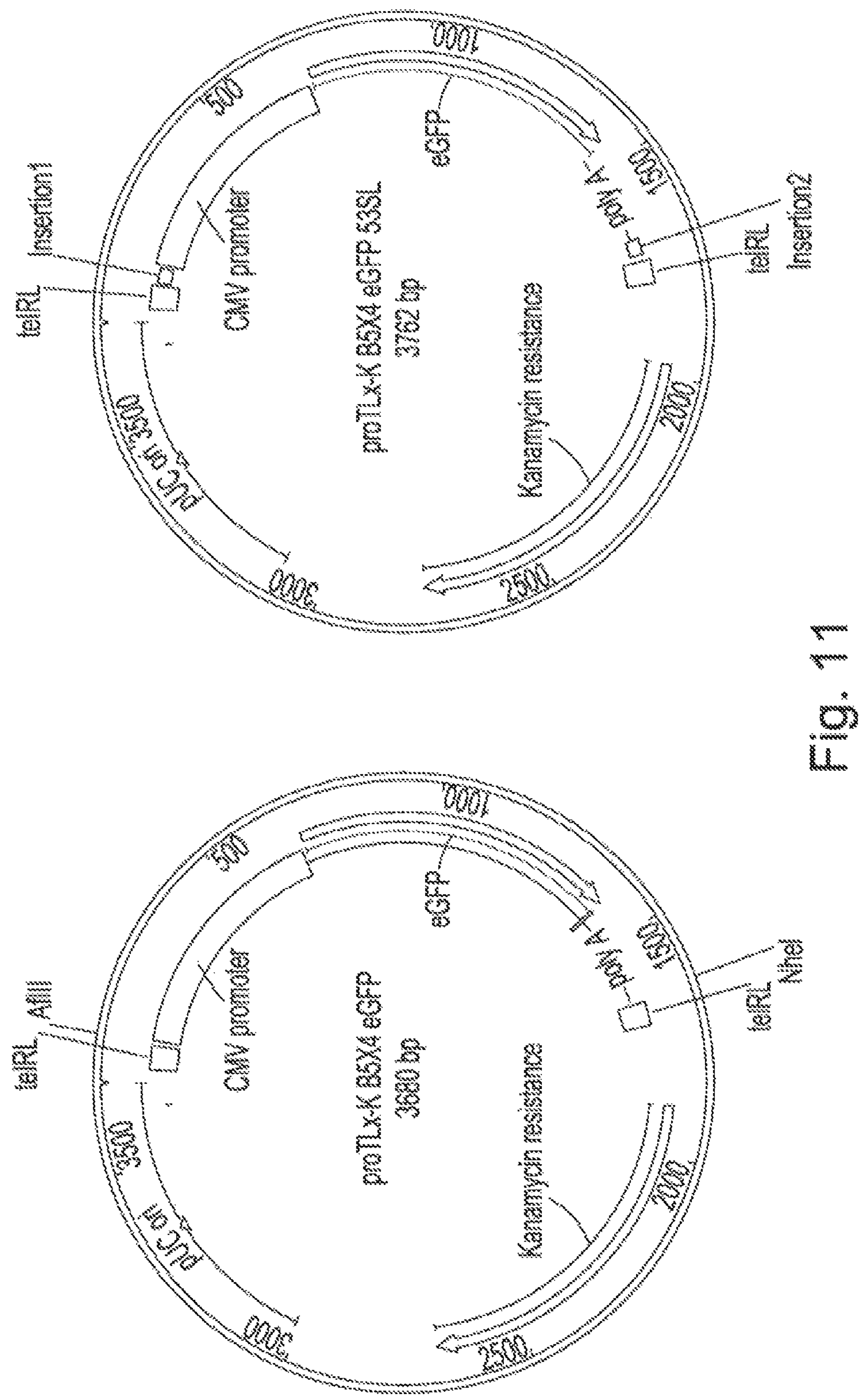

FIG. 10A shows the linear sequence of introduced stem loop used in Example 1. This also shows the primers used in Example 1 and the binding position in the loop is shown. FIG. 10B is a photograph of an 0.8% agarose gel of TelN digest of amplified products produced from different priming strategies;

FIG. 11 depicts a plasmid map for the vectors used in Example 1. Various components are depicted.

Figure 12:
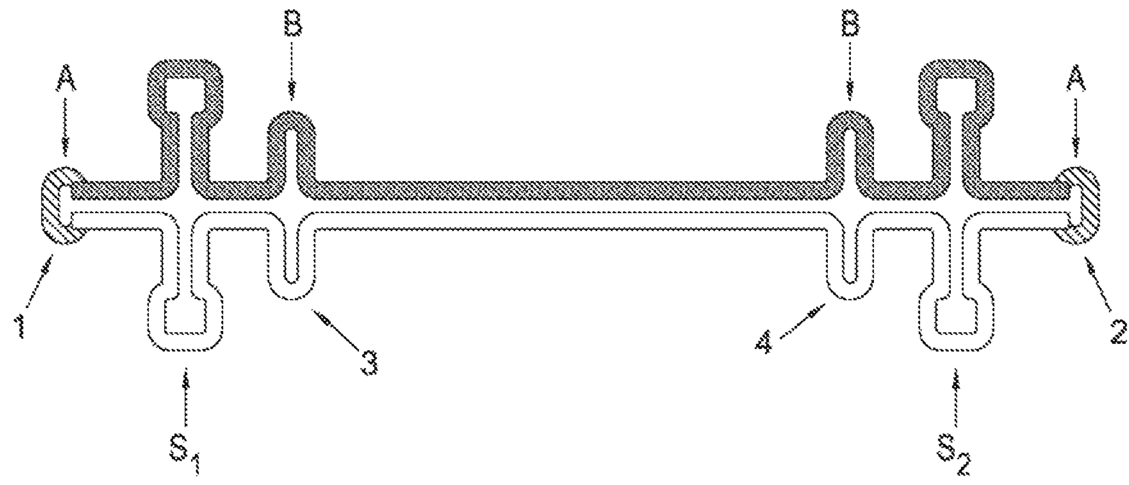

FIG. 12 depicts an exemplary structure of a closed linear DNA template comprising recognition sequences from two different protelomerases separated by a stem loop motif (S1 indicates the complementary stem loop pair that is created at one position due to the stem loop motif, and S2 indicates a second stem loop pair created at a different position due to a further stem loop motif that can be the same or different) incorporating a primer binding sequence. The primer can be designed to bind to either one of the pair. The closed ends of the linear DNA are formed by two portions of the same protelomerase recognition sequence, in this example, protelomerase A. An additional pair of protelomerase B recognition sequences is present within the double stranded section as a complete site capable of being cleaved and ligated by protelomerase B. It will be understood that sequences 1, 2, 3, and 4 could be protelomerase recognition sequences for the same or a mixture of different protelomerase enzymes.

Figure 13:
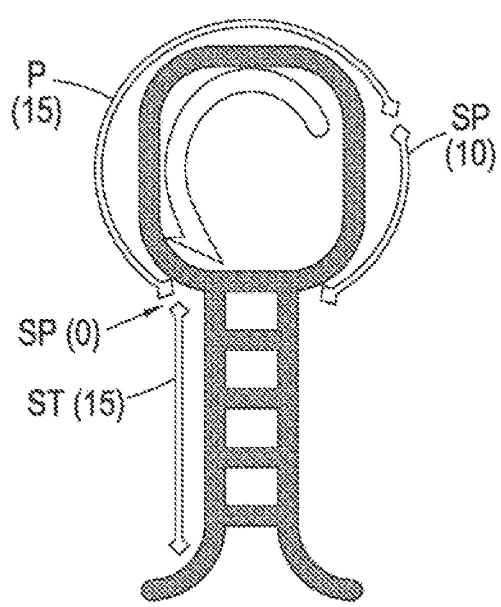

FIG. 13 shows the structure of an exemplary stem loop motif 15-0-15-10, with the priming site held in the open configuration. The naming scheme refers to the length of the stem (ST) (15), the length of the first spacer (SP) (0), the length of the priming site (P) (15), the length of the second spacer (SP) (10). The primer may bind to the top strand. A loop labelled 'reverse' is the same sequence on the opposite strand, with the primer binding to the bottom strand. The scheme could use any suitable length of sequence for any of the elements depicted.

Figure 14:
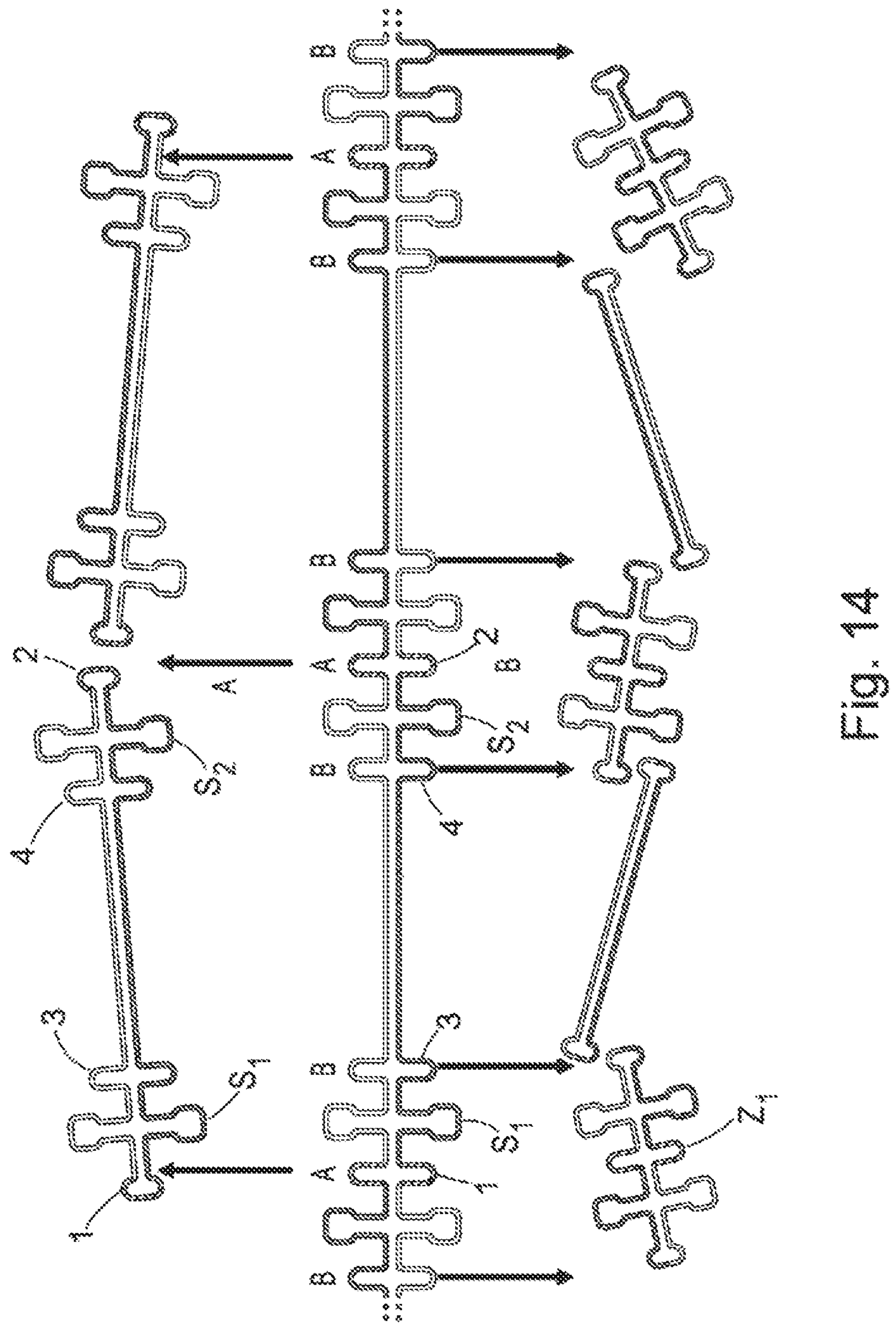

FIG. 14 depicts a process according to one aspect of the present invention when the template of FIG. 12 is used. The central molecule of the figure shows a section of double stranded concatameric product produced by rolling circle amplification of template depicted in FIG. 12. In this instance, the single strand that rolls off the template depicted in FIG. 12 has been converted into a double stranded concatamer through synthesis of a complementary strand, which has been enabled due to the use of the stem loop motifs. This figure depicts the stem loop motifs as complementary stem sequences supporting open single stranded sections that are available for primer binding and further amplification by a strand displacing DNA polymerase. In this instance, protelomerase recognition sequences 1 and 2 are both sequences for Protelomerase A, and protelomerase recognition sequences 3 and 4 are both sequences for Protelomerase B. Both protelomerase recognition sequences A and B are capable of being cleaved and ligated by their respective protelomerases. Cleavage with protelomerase A (top of figure) yields a closed linear DNA identical to the template as depicted in FIG. 12. Cleavage and ligation with protelomerase B (bottom of figure) yields a closed linear DNA capped by protelomerase B recognition sequences and free from protelomerase A recognition sequences and stem loop motifs. Additionally a very short waste closed linear DNA (Z1) is produced also capped by protelomerase B recognition sequences and incorporating the stem loop motifs and a single protelomerase A recognition sequence. Therefore, the skilled person can select which product is produced by varying the protelomerase added to the process. S1 indicates the complementary stem loop pair that is created at one position due to the stem loop motif, and S2 indicates a second stem loop pair created at a different position due to a further stem loop motif that can be the same or different.

Figure 15:
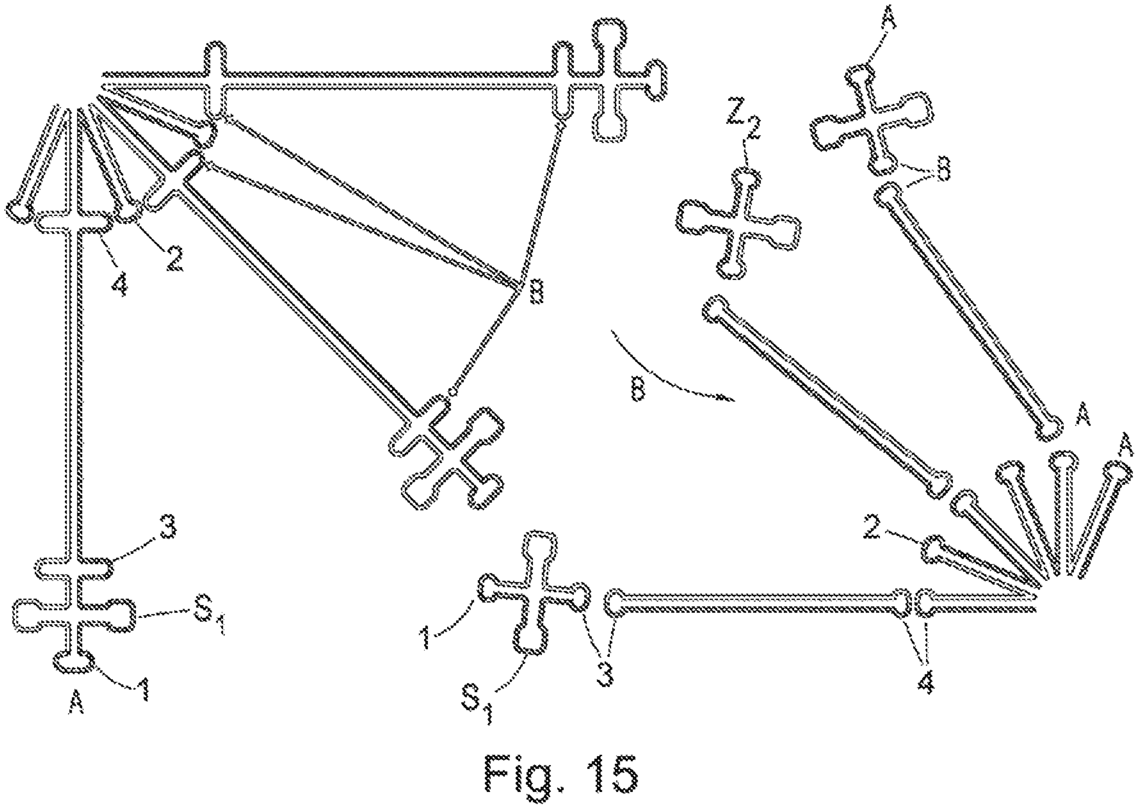

FIG. 15 shows a section of a single stranded concatameric product produced by rolling circle amplification of the closed linear DNA template depicted in FIG. 12. This figure shows how single stranded concatamers are able to fold internally to form nanoflowers if they are not immediately converted into double strands through synthesis of a complementary DNA strand. DNA nanoflowers formed in this way from a closed linear DNA template with additional protelomerase recognition sequences can be directly converted into closed linear DNA including a target sequence by treatment with protelomerase B. Such a closed linear DNA product does not contain any stem loop sequences or protelomerase A recognition sequences (sequences 1 and 2). It should be noted that the second stem-loop structure is not depicted in this figure, since it is thought that these will not form at the nested end, as the inventors assume that adjacent complementary sequences hybridise before separated ones. A small percentage of ends may allow for the formation of stem loops, but the structure depicted is more likely and energetically favourable. This Figure shows one embodiment where a sole primer is used. If an alternative primer is used (i.e. for a different stem loop) then alternative side products (Z2 in this embodiment) may be formed.

Figure 16:
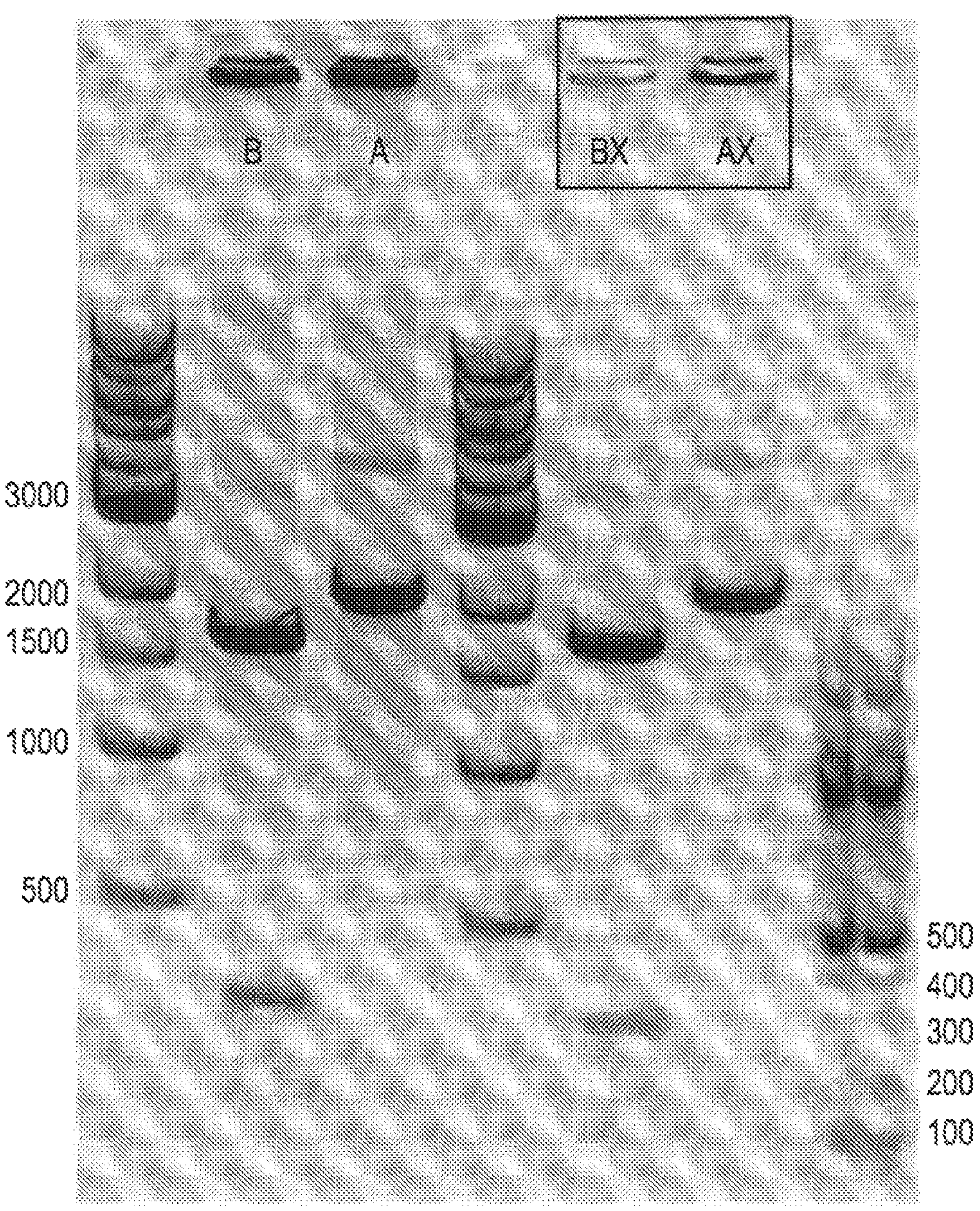

FIG. 16 depicts a gel showing successful cleavage of nanoflowers formed from single stranded concatamers and the cleavage of double stranded concatamers. Lane 'B' is the product of rolling circle amplification cleaved with TelN, showing waste products from cleavage of double stranded concatamers (~300 bp and Z1 on FIG. 14) and nanoflowers (~150 bp and Z2 on FIG. 15) as well as closed linear DNA product (~1600 bp). Lane 'A' shows cleavage of the same reaction with VP58.5, showing full-length template product (~1900 bp) and more uncleaved DNA in wells. Lanes BX and AX show the results of incubation with an exonuclease.

Figure 17:
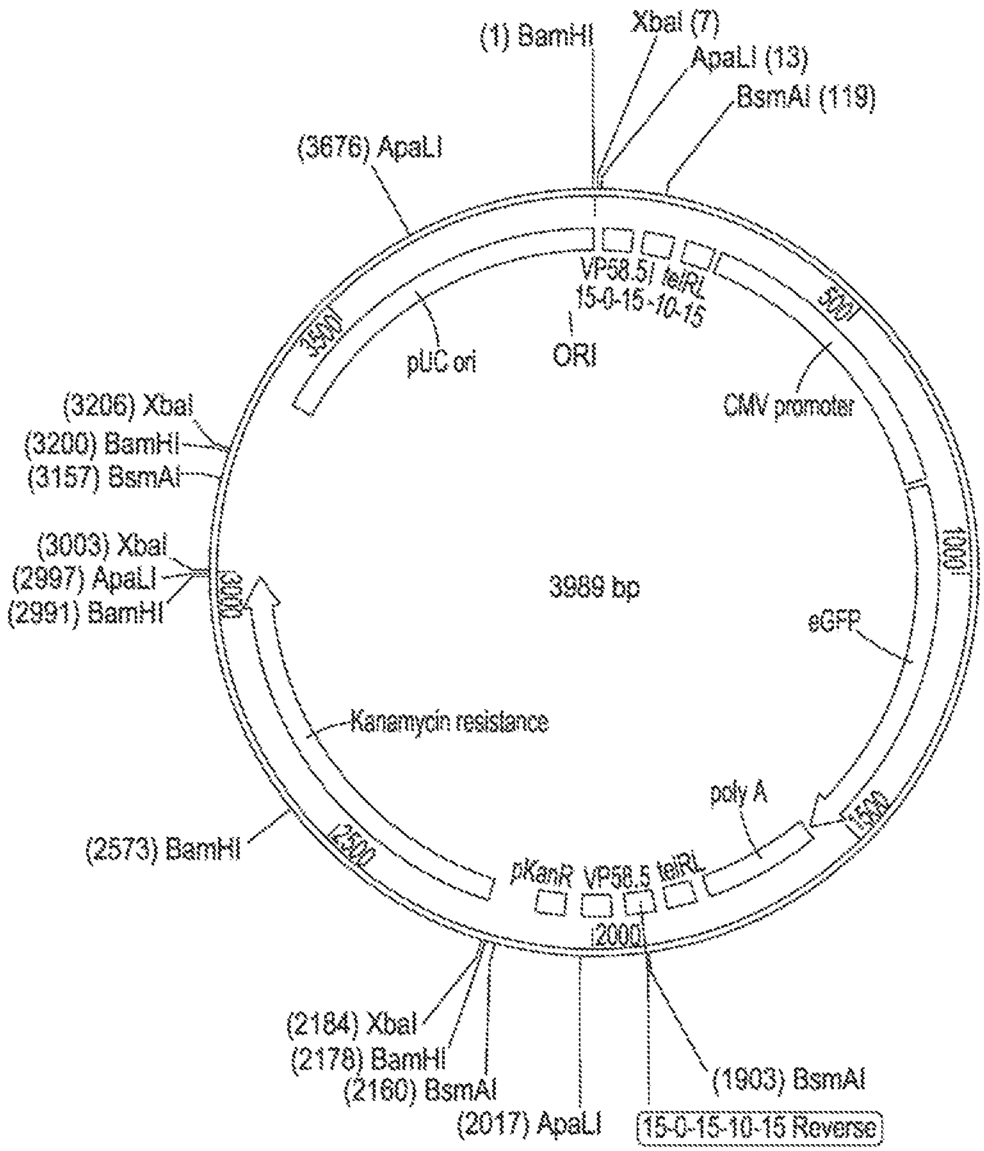

FIG. 17 depicts a map of the plasmid used in Example 2 (proTLx-K B5X4A4 eGFP 15-0-15-10) with the key components depicted. TelRL and VP58.5 represent the recognition sequences for protelomerases TelN and VP58.5 respectively. The sequence depicted as 15-0-15-10-15 and located between teIRL and VP58.5 represents the stem loop motif containing an open primer binding site (see FIG. 13).

DETAILED DESCRIPTION

The present invention relates to improved, cell-free processes for synthesising or amplifying closed linear DNA from a closed linear DNA template.

The Closed Linear DNA Template

The DNA template for use in the method of the invention has certain features which are pertinent, and these are described further below. Closed linear DNA, i.e. linear double stranded covalently closed DNA molecules; typically comprise a linear double stranded section of DNA with covalently closed ends, i.e. hairpin ends. The hairpins join the ends of the linear double DNA strands, such that if the molecule was completely denatured, a single stranded circular DNA molecule would be produced.

Figure 2:
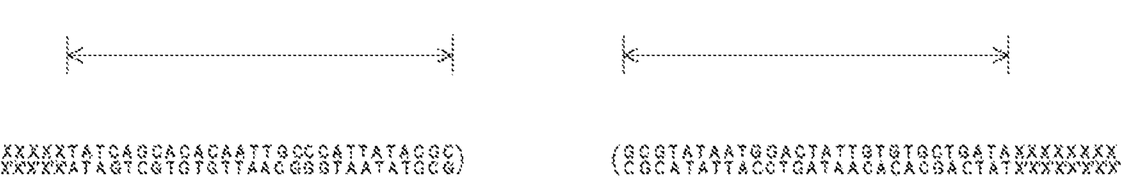
FIG. 2 shows what happens to the sequence of FIG. 1 (SEQ ID NO: 15) once protelomerase TelN catalyses the reaction at the recognition sequence. The sequence (SEQ ID NO:15) is cleaved at the point indicated (D on FIG. 1) to form the cleaved ends of SEQ ID NO: 15 shown in FIG. 2 as sequences on the left and right sides of the figure, and the each cleaved ends are re-ligated with the opposing strand to form two separate hairpin structures.
Figure 3:
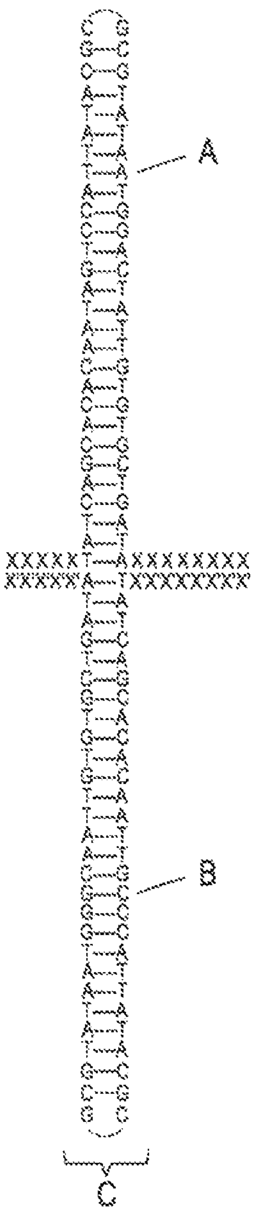
FIG. 3 depicts the same sequence as FIG. 1 (SEQ ID NO: 15), but demonstrates that the portions of the protelomerase recognition sequence (A and B) may form internal hairpins, rather than bind to the other portion of the protelomerase recognition sequence, despite being complete (C)
Figure 5:
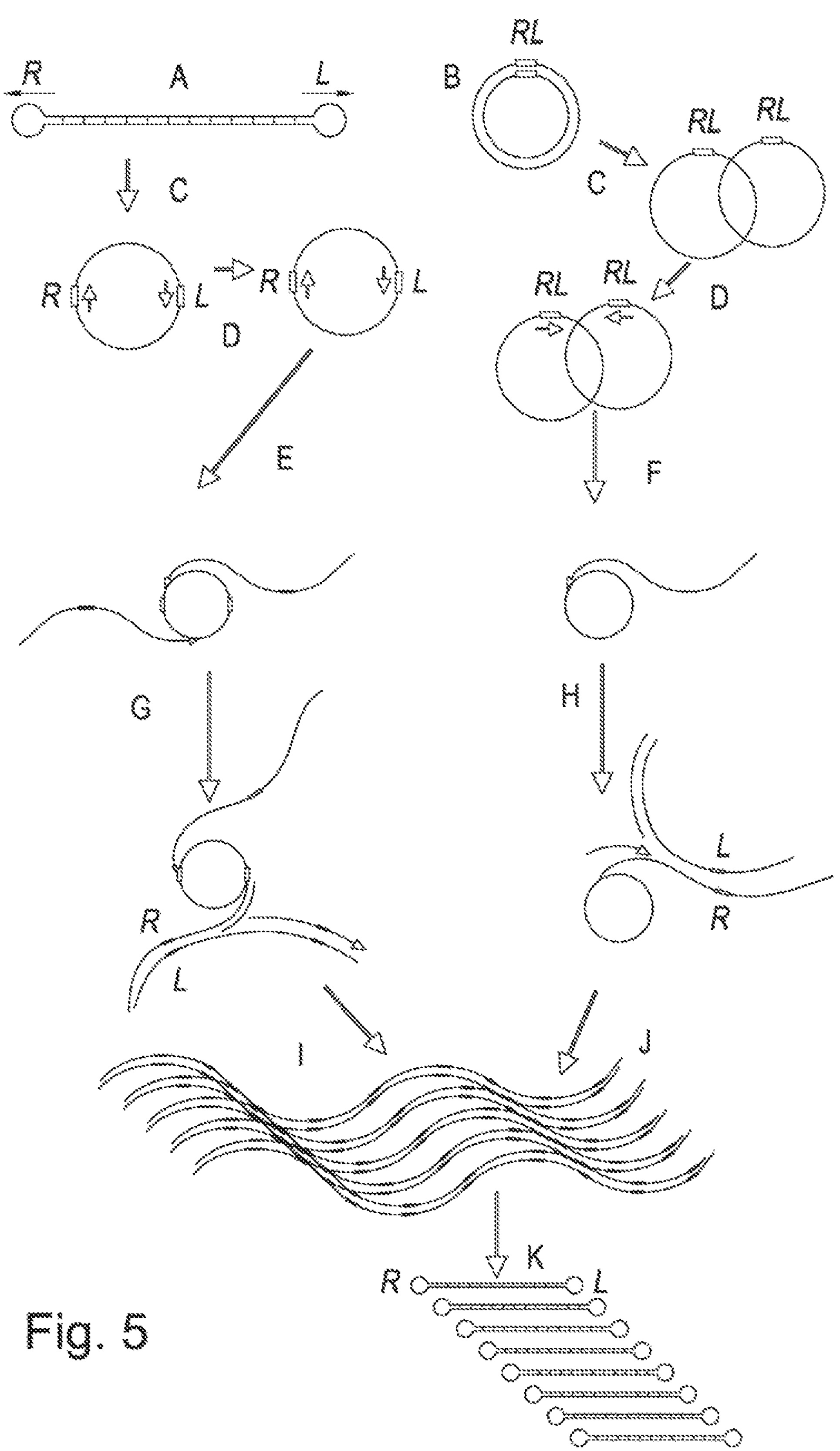
FIG. 5 shows the ideal specific process for in vitro manufacture of closed linear DNA using a single specific palindromic primer, a closed linear DNA template and a strand displacement DNA polymerase in combination with TelN protelomerase. A. Closed linear DNA template. R and L represent the DNA sequences of the right and left arms of the TelN protelomerase recognition sequence. B. Plasmid DNA template. C. Denaturation of starting template to form circular single stranded DNA. Since the plasmid DNA template is comprised of catenated rings of single stranded DNA, it will be understood that the single stranded circles cannot be separated. These 'catenanes' or topologically interlinked circles are not covalently linked, but cannot be separated because they are interwound and each is covalently closed. D. Binding of single specific primer. E-H. Amplification from single stranded DNA template by a strand displacement DNA polymerase. H. Formation of long concatameric double stranded DNA comprising single units of amplified template separated by protelomerase binding sequences (RL). K. Contacting with TelN protelomerase specific to RL sequence. Protelomerase cleaves concatameric DNA at RL site and ligates complementary strands to produce amplified copies of the linear covalently closed DNA template.
Figure 6:
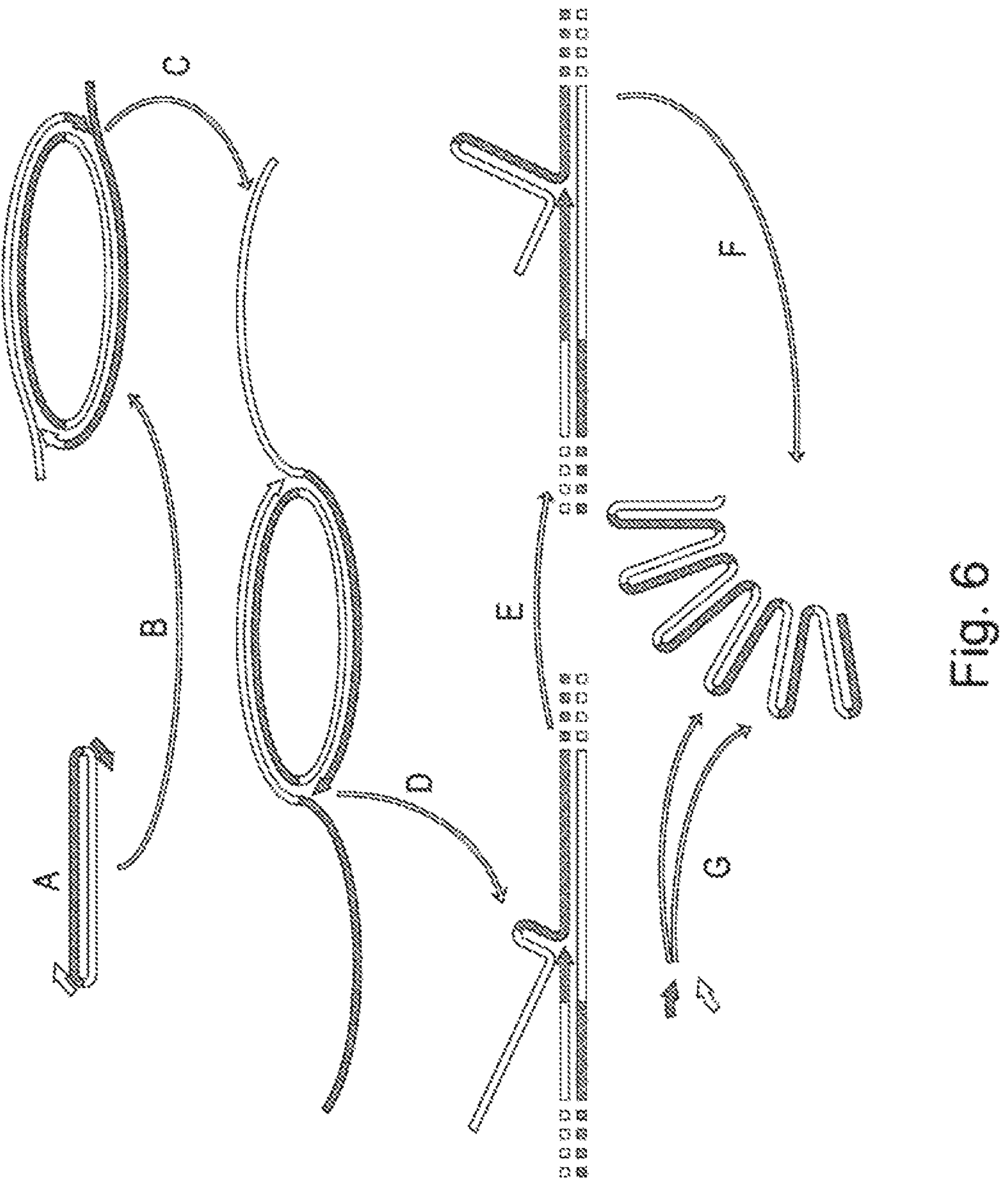
FIG. 6 shows the same process as FIG. 5, only instead of forming long concatameric double stranded DNA, the concatameric single strand of DNA folds into DNA nanoflowers; A. Closed linear DNA template; B-C. Specific primer binding and amplification from single stranded DNA template by a strand displacement DNA polymerase and formation of long concatameric single strands of DNA, although two primer species are shown in this embodiment they are identical, but the method could be performed with two or more different primer species. D-E. Specific primer binding to the concatameric single strand of DNA and replication of the same, leading to hairpin formations at the portions of the protelomerase recognition sequences. F-G. the formation of DNA nanoflowers made from concatameric single strand of DNA, to which primers are unable to bind.
Figure 7:
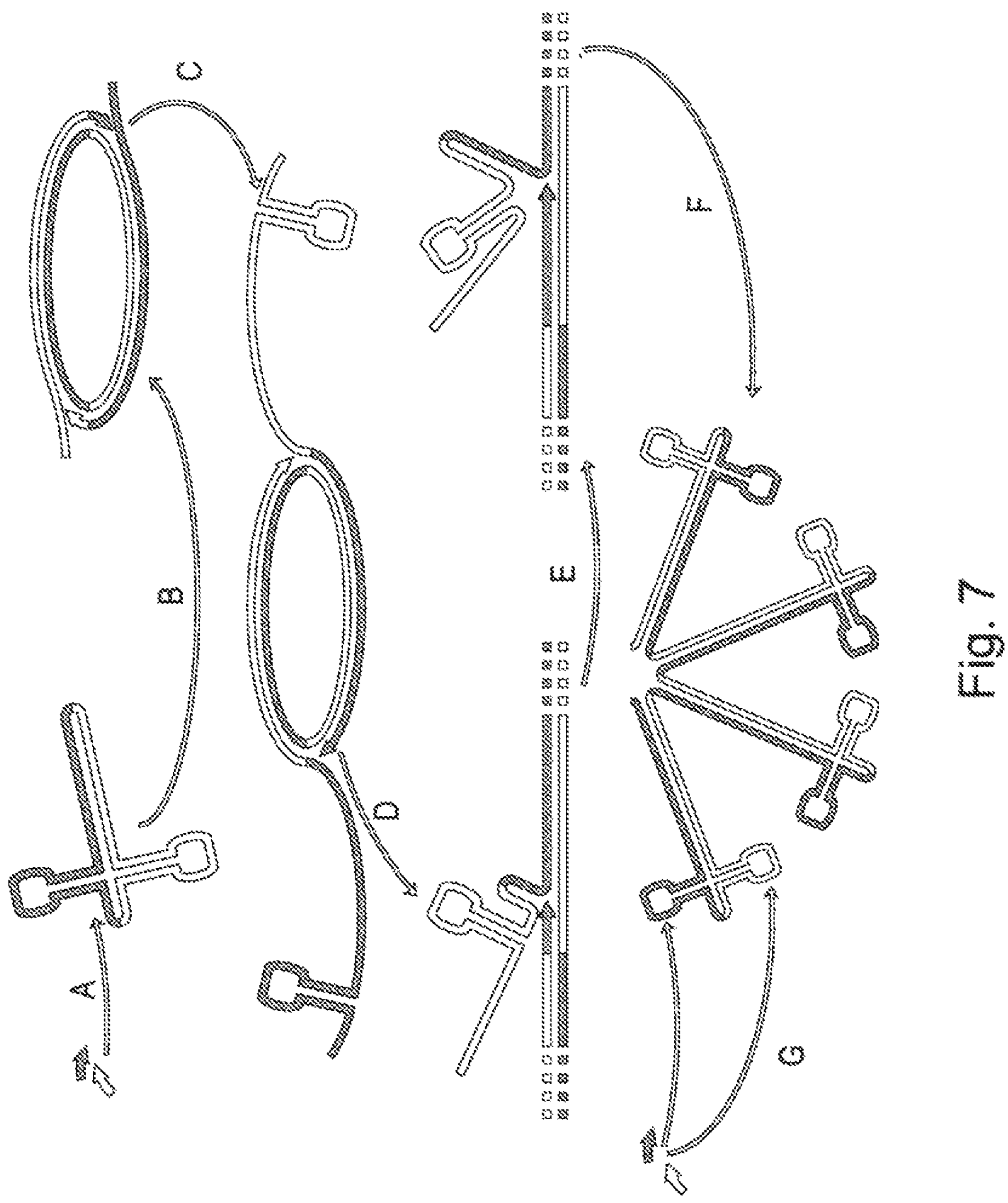
FIG. 7 shows the same general process as FIGS. 5 and 6, with the exception that the closed linear DNA template includes a stem loop motif according to the present invention. This stem loop motif includes a primer binding site, and is particularly designed so that the stem loop structure is formed when the sequence for the motif is single stranded; thus forming in the concatameric single strands of DNA.

For the purposes of this invention, the covalently closed ends or hairpins contain internally complementary sequences, since they comprise a part or a portion of a protelomerase recognition sequence. The bases within the apex (end or turn) of the hairpin may not be able to form base pairs, due to the conformational stress put onto the DNA strand at this point. FIG. 3 shows that it is thought that at least the 2 base pairs at the apex of the portion of the protelomerase recognition sequence may not form base-pairs, but the exact conformation is not yet known and likely to be subject to fluctuations depending on the conditions in which the DNA is maintained, and the exact sequences around the hairpin. Thus, 2 or more bases may not be able to form pairs given the structural distortion involved, despite their complementary nature. FIG. 2 showing the hairpins created by the action of the protelomerase TelN on the TelRL site. Some "wobbles" of non-complementary bases within the length of a hairpin may not affect the structure. A wobble may be a break in the palindrome, but the sequences may remain complementary. It is, however, preferred that the sequence of the hairpin is entirely self-complementary. Each protelomerase enzyme, working on its appropriate protelomerase recognition sequence, will generate two different hairpins at the end of the closed linear DNA if there are 'wobbles' in the palindrome. FIG. 2 illustrates this point with both an "R" and an "L" hairpin being generated.

Complementarity describes how the bases of each polynucleotide in a sequence (5' to 3') are in a hydrogen-bonded pair with a complementary base, A to T (or U) and C to G on the anti-parallel (3' to 5') strand, which may be the same strand (internal complementary sequences) or on a different strand. This definition applies to any aspect or embodiment of the invention. It is preferred that the sequences in the hairpin are 90% complementary, preferably 91%, 92%, 93%, 94%, 95%, 96%, 98%, 99% or 100% complementary.

Thus, the DNA template comprises a linear double stranded DNA closed at each end with a portion of a protelomerase recognition sequence. Each end may be formed of a portion of a protelomerase recognition sequence for the same or different protelomerase enzymes. These portions may be named as the first and second protelomerase recognition sequences, and these form the ends of the closed linear DNA template.

The DNA template may comprise further protelomerase recognition sequences, in addition to those at the closed ends (the first and second protelomerase recognition sequences). These further protelomerase recognition sequences are positioned in the double stranded section of the closed linear DNA. There may be one, two or more protelomerase recognition sequences present within the double stranded section. These sequences may be named the third, fourth, fifth, sixth, or "nth" protelomerase recognition sequences. Each may be a protelomerase recognition sequence for the same or different enzyme. It is preferred that the additional or further protelomerase recognition sequences are different to those used to cap the end of the closed linear DNA template (the first and second protelomerase recognition sequences which are independently the same or different—shown as both the same and labelled "A" in FIG. 12).

The additional protelomerase recognition sequences may be positioned at any point in the double stranded DNA segment of the closed linear DNA template. The additional protelomerase recognition sequences are distinct to the stem loop motif, they are not the same entity, since protelomerase recognition sequences cannot fold to form a stem loop as defined herein. It is preferred that, if additional protelomerase recognition sequences are present, that they are separated from the closed ends of the template by a stem loop motif. In this embodiment, it is preferred that there are two additional protelomerase recognition sequences, which are the same or different, and which are separated from the closed ends of the template DNA by a stem loop motif.

Thus, an exemplary template comprises a linear, double stranded DNA molecule covalently closed at each end by a portion of a first and a second protelomerase recognition sequence; and comprising at least two stem loop motifs and at least a third and a fourth protelomerase recognition sequence, wherein the first of said stem loop motifs is between the first and third protelomerase recognition sequences and the second of said stem loop motifs is between the fourth and second protelomerase recognition sequences. In other words, each stem loop motif is positioned between the capped end of the closed linear DNA and the additional protelomerase recognition sequence. This is depicted in FIG. 12.

A protelomerase recognition sequence is any DNA sequence whose presence in a DNA sequence allows for its conversion into a closed linear DNA by the enzymatic activity of protelomerase. In other words, the protelomerase recognition sequence is required for the cleavage and religation of double stranded DNA by protelomerase to form covalently closed linear DNA. Typically, a protelomerase recognition sequence comprises a palindromic sequence i.e. a double-stranded DNA sequence having two-fold rotational symmetry, also described herein as an inverted repeat. The length of the inverted repeat differs depending on the specific organism from which the protelomerase is derived. The palindrome or inverted repeat may be perfect or imperfect. A complete protelomerase recognition sequence preferably comprises a double stranded palindromic (inverted repeat) sequence of at least 14 base pairs in length.

In more detail, a complete protelomerase recognition sequence is recognised and cleaved by its cognate protelomerase, and can be presented as a duplex of a first DNA sequence comprising a forward (or sense) portion of a protelomerase recognition sequence and a complementary second DNA sequence containing the reverse (or antisense) portion of the protelomerase recognition sequence. Once the recognition sequence has been cleaved, what is left behind is a portion or part of the protelomerase recognition sequence. The portion or part is preferably a single strand of the entire sequence, which when paired with its complementary sequence, forms a complete recognition sequence in a double stranded format. Thus, the portion may be the forward (or sense) portion of the protelomerase recognition sequence or the reverse (or antisense) portion.

The length of the first or second portion of the protelomerase recognition sequence is determined by the minimum sequence recognised by the cognate protelomerase in order to bind, cleave and re-join the free ends. Several complete protelomerase recognition sequences are depicted in FIG. 4, and each strand represents a portion of the recognition sequence for the cognate protelomerase. The length of the portion of the protelomerase recognition sequence for a cognate protelomerase may be the same or nearly so, since they are capable of annealing to form a duplex. Each portion of a protelomerase recognition sequence may be 20 to 100 bases in length, more particularly 30 to 100 bases in length.

Figure 1:
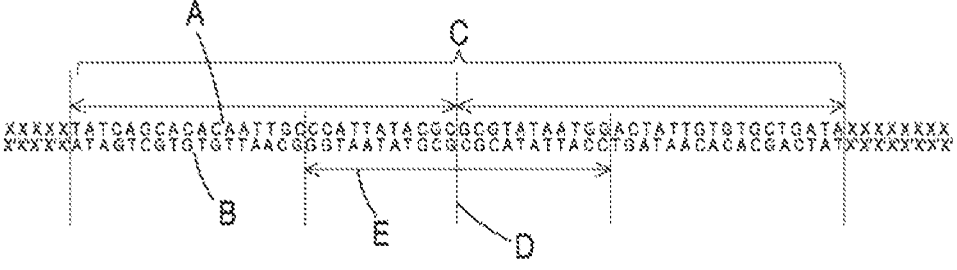
FIG. 1 shows the sequence of the protelomerase recognition sequence for protelomerase TelN in a linear format, without the hairpin structures (SEQ ID NO: 15). It can be seen that the first portion of the protelomerase recognition sequence (A) has a sequence which is complementary to the second portion of the protelomerase recognition sequence (B). At the centre (in this example) of the protelomerase recognition sequence (D) is the site at which the protelomerase will cleave the sequence, which is in the centre of the telO sequence (E). The complete protelomerase recognition sequence (C) is composed of TelRL for the enzyme TelN.

As shown in FIG. 1, despite the two portions (A and B) of the protelomerase recognition sequence (C) forming a duplex due to the complementary nature of the sequence of the portions, because of the palindromic nature of the protelomerase recognition sequence, each portion has the ability to fold into a hairpin due to internal self-complementary sequences within the portion of the recognition sequence. This is shown in FIG. 3.

The closed linear DNA template according to the present invention comprises a sequence for a stem loop motif within the linear double stranded DNA. As used herein, a stem loop motif is a sequence that allows for the formation of a stem loop structure, under the appropriate conditions. The sequence of the stem loop motif may comprise a central section flanked by two additional sequences.

The sequence for the stem loop motif may include a central section which forms the loop structure of the stem loop. This central section (loop) is thus designed to be single-stranded and not be complementary to any of the other bases within the motif. This central section may be any appropriate number of residues in length, but it is preferred that the central section (and hence the loop) is 5 to 50 residues, particularly 5 to 40 residues, more particularly 5 to 30 residues, even more particularly 10 to 25 residues in length. The central section, and thus the loop, may be 5, 6, 7, 8, 9, 10, 11, 12, 13, 14, 15, 16, 17, 18, 19, 20, 21, 22, 23, 24, 25, 26, 27, 28, 29 or 30 residues (bases) in length.

Preferably, the central section of the motif or loop includes a sequence for a primer binding site. A primer binding site is a region of a nucleotide sequence where a primer binds or anneals to start replication. The primer specifically anneals to the primer binding site due to the complementary nature of their sequences. The primer binding site may be designed such that primers can anneal which are complementary to a part or portion of the primer binding site, see for example FIG. 10A Alternatively, the primer binding site and primer may be the same length. Primer design, and thus the sequence of the primer binding site are discussed in more detail further below. The primer binding site is at least 5 residues in length, but can be 5 to 50 residues (bases) in length. Ideally, the primer binding site is 5 to 30 or 5 to 20 residues in length, optionally 5 to 16 residues in length. The primer binding site may be at least 5, 6, 7, 8, 9, 10, 11, 12, 13, 14, 15, 16, 17, 18, 19, 20, 21, 22, 23, 24, 25, 26, 27, 28, 29 or 30 residues in length. It is preferred that the primer binding site forms a part or portion of the central section, adjoined by at least one sequence which separates the primer binding site from the flanking sequences. The adjoining sequence may be present on the 3' or 5' side of the primer binding site, or be present on both sides of the primer binding site. The adjoining sequences may be of any suitable length, and each of the adjoining sequences is independent—i.e. the presence, length or nature of the adjoining sequence may be different on either side of the primer binding site, if present. Each adjoining sequence may be up to 50 residues in length, preferably up to 40, up to 30 or up to 20, most preferably, 15 residues in length. The adjoining sequences may therefore be at least 1, 2, 3, 4, 5, 6, 7, 8, 9, 10, 11, 12, 131, 14, 15, 16, 17, 18, 19 or 20 residues (bases) in length.

FIG. 13 depicts an exemplary stem loop structure with the format 15-0-15-10, with the priming site held in the open configuration. The naming scheme refers to the length of the stem (15), the length of the first spacer (0), the length of the priming site (15), the length of the second spacer (10). It will be understood that this format could be followed using elements of different lengths to those depicted.

In one embodiment, a stem loop structure may occur due to intramolecular base pairing within a single strand of DNA. In this instance, the stem loop occurs when two regions of the same strand, usually complementary in nucleotide sequence when read in opposite directions, base-pair to form a double stranded section that ends in an unpaired loop. Alternatively, in a second embodiment, the stem loop motif may include sequences which are acted upon by oligonucleotide bridging molecules, which force a section of DNA into a single stranded loop.

The sequence for the stem loop motif may include two complementary regions flanking the central non-complementary loop section. Complementarity is defined previously. Thus, for example, a sequence for a stem loop motif reads (5' to 3'): 5' flanking sequence, central section, 3' flanking sequence. The 5' and 3' flanking sequences are complementary when the 3' flanking sequence is read 3' to 5'. This enables the flanking sequences to base pair to each other and form a duplex, with the central section looping out as a single strand between them. In this embodiment, the flanking sequences are of the same or very similar length. The flanking sequences are preferably at least 5 residues (bases) in length, or at least 6, 7, 8, 9 or 10 residues in length. The flanking sequences may be up to 10, 15, 20, 25, 30, 35, 40, 45 or 50 residues in length. Where the flanking sequences are designed to be self-complementary, it will be appreciated that the stability of double stranded section is determined by its length, the number of mismatches it contains (a small number are tolerable) and the base composition of the paired region. Pairings between guanine and cytosine have three hydrogen bonds and are more stable compared to adenine-thymine pairings, which have only two. Those skilled in the art will appreciate how to design a sequence for a stem loop motif such that the structure, when formed, is stable. The Integrated DNA Technologies Oligo-analyzer may be used in order to determine the suitability of stem loop structures. Version 3.1 is available at https://www.idtdna.com/calc/analyzer.

In an alternative embodiment, the sequences flanking the central section are designed such that they are at least partially complementary to a bridging oligonucleotide. Complementarity is as defined previously. In this embodiment, the flanking sequences are designed to be brought together as an essentially contiguous sequence bound to a bridging oligonucleotide, forcing the central section to loop out between the flanking sequences. Thus, in this embodiment, the flanking sequences are designed to be complementary in sequence to a bridging oligonucleotide. The flanking sequences are preferably at least 5 residues (bases) in length, or at least 6, 7, 8, 9 or 10 residues in length. The flanking sequences may be up to 10, 15, 20, 25, 30, 35, 40, 45 or 50 residues in length. Thus the sequence for a stem loop motif may enable the formation of a stem loop in that sequence, and/or the complementary sequence thereof, under appropriate conditions. Such conditions can include the presence of the sequence for the stem loop motif within a single strand of DNA, such as the single strand that is produced during replication of the template. Alternative conditions in which the stem loop may form is denaturation/renaturation conditions mediated by changes in pH, temperature and ionic environments. It is preferred that the conditions for the formation of the stem loop are those used for the amplification of the DNA template, such that the stem loop structures are formed immediately or shortly after they are incorporated into the synthesised single strand of DNA by the DNA polymerase.

It will be understood by those skilled in the art that the sequence for the stem loop motif, when present in the template, will be present on both the forward (sense) and reverse (antisense) strands (as mirror images/complementary sequences). In a closed linear DNA template the forward and reverse strands are formed of one circular strand of DNA.

When the template is replicated in the method of the invention, the sense sequence replicates to provide an antisense sequence, and the antisense sequence replicated to provide the sense sequence. Thus, there is always a sense and antisense version of the sequence for the stem loop motif in both the template and the replicated DNA. The replicated DNA is a single stranded concatamer, which will comprise both the sense and antisense sequence on the same strand of DNA.

Both the sense and antisense sequences may be capable of forming a stem loop structure. In the closed linear DNA template, this can result in a paired stem loop structure as shown in FIG. 9B, each of the pair being on opposite sides of the double stranded section of the closed linear DNA. In the replicated DNA, the single stranded concatamer, paired stem loops structures may also form as shown in FIG. 9D. These paired stem loops serve to maintain an open priming site within the DNA nanoflower that forms due to the nature of the DNA sequence being replicated.

A primer may be designed to bind to either the sense or antisense version of the "primer binding site". The method of the present invention requires at least one primer. Optionally, the sequence of the primer binding site is in the correct format (direction) in the sense version/sequence of the stem loop motif. Thus, one option is that the primer anneals to the primer binding site on the sense version of the sequence from the stem loop motif. Clearly, the system can be designed in reverse and the primer may be designed to be able to bind to the primer binding site on the antisense version of the sequence from the stem loop motif. Since both are present in both the template and the replicated DNA, either sequence is available for annealing. Thus, when the method of the invention is performed with sole species of primer it can be designed to anneal to either the sense or antisense version of the primer binding site. If the method of the invention is performed with two or more primers, each primer can be individually designed to bind to either the sense or the antisense version of the sequence for the stem loop motif.

The stem loop motif sequence includes a sequence to form a single stranded loop. As such, it should be noted that the stem loop motif is not a portion of a protelomerase recognition sequence, since this includes no sequence for a loop. Thus, the stem loop motif is distinct from said protelomerase recognition sequence or a portion thereof, and therefore distinct from the closed or capped ends of the closed linear DNA.

The closed linear DNA may comprise one or more sequences comprising a stem loop motif, thus may comprise 2, 3, 4, 5, 6, 7, 8, 9, or 10 such motifs. The stem loop motif may be included at any appropriate location in the closed linear DNA section. Optionally, the stem loop motif sequence is included adjacent to the portion of a protelomerase recognition sequence which forms a covalently closed end. Adjacent in this context can be within 1-100 residues of the end of the portion of the protelomerase recognition sequence, optionally within 1, 2, 3, 4, 5, 6, 7, 8, 9, 10 11, 12, 13, 14, 15, 16, 17, 18, 19 or 20 residues of the end of the protelomerase recognition sequence portion. Alternatively, the two entities may be near to each other, i.e. up to 25, 30, 35, 40, 45, 50, 55, 60, 65, 70, 75, 80, 85, 90, 95 or up to 100 residues apart (can be measured from the end of the protelomerase recognition sequence portion to the start of the stem loop motif, or vice versa).

The closed linear DNA template may further comprise any sequence within the double stranded sequence, either naturally derived or artificial. It may comprise at least one processing enzyme target sequence, such as one, two, three, four or more processing enzyme target sites. Such a target sequence is to allow for the DNA to be optionally processed further following synthesis. A processing enzyme is an enzyme that recognises its target site and processes the DNA. The processing enzyme target sequence may be a target sequence for a restriction enzyme. A restriction enzyme, i.e. a restriction endonuclease, binds to a target sequence and cleaves at a specific point. The processing enzyme target sequence may be a target for a recombinase. A recombinase directionally catalyses a DNA exchange reactions between short (30-40 nucleotides) target site sequences that are specific to each recombinase. Examples of recombinases include the Cre recombinase (with loxP as a target sequence) and FLP recombinase (with short flippase recognition target (FRT) sites). The processing enzyme target sequence may be a target for a site-specific integrase, such as the phiC31 integrase.

The processing enzyme target sequence may be a target sequence for a RNA polymerase, such that the DNA becomes a template for polypeptide synthesis. In this instance, the processing enzyme targeting site is a promoter, preferably a eukaryotic promoter.

The closed linear DNA template may comprise one or more further protelomerase recognition sequences, in addition to those present at the closed ends of the template. These sequences may be any protelomerase recognition sequences, but are preferably different to the first and second protelomerase recognition sequences used in the closed linear ends of the template. They may also be the same or different to each other. It is preferred that at least two additional protelomerase recognition sequences are present, and are included within the double stranded section of the closed linear DNA in a pair. This pair of protelomerase recognition sequences (the third and fourth sequences) may flank a desired sequence in the closed linear DNA template. It is preferred that this desired sequence does not include a stem loop motif as defined herein. The desired sequence may include an expression cassette, or any other sequence of interest. The desired sequence may be the sequence for a closed linear DNA to be produced using the methods of the invention. In this instance, the third and fourth protelomerase recognition sequences are necessary for the formation of the closed ends of the closed linear DNA, with the desired sequence forming the double stranded section. The third and fourth sequences may be sited adjacent to or near the stem loop motifs. In one embodiment, a stem loop motif separates a protelomerase recognition sequence from the nearest closed end. In another embodiment, there are a pair of additional protelomerase recognition sequences, and each are separated from a closed end by a stem loop motif.

The closed linear DNA template may comprise an expression cassette comprising, consisting or consisting essentially of a eukaryotic promoter operably linked to a sequence enclosing a protein of interest, and optionally a eukaryotic transcription termination sequence. A "promoter" is a nucleotide sequence which initiates and regulates transcription of a polynucleotide. "Operably linked" refers to an arrangement of elements wherein the components so described are configured so as to perform their usual function. Thus, a given promoter operably linked to a nucleic acid sequence is capable of effecting the expression of that sequence when the proper enzymes are present. The term "operably linked" is intended to encompass any spacing or orientation of the promoter element and the DNA sequence of interest which allows for initiation of transcription of the DNA sequence of interest upon recognition of the promoter element by a transcription complex.

The DNA template may be of any suitable length. Particularly, the DNA template may be up to 100 kilobases, or up to 50 kilobases, or up to 40 kilobases, or up to 30 kilobases. Preferably the DNA template may be 100 bases to 100 kilobases, 200 bases to 40 kilobases, more preferably 200 bases to 30 kilobases, most preferably 1 kilobases to 15 kilobases.

The closed linear DNA template as used in the method of the invention is unique. Thus, according to a third aspect, the invention relates to a double stranded DNA molecule covalently closed at each end by a portion of a protelomerase recognition sequence, wherein the sequence of said linear, double stranded DNA molecule includes at least one stem loop motif. All these elements have been defined above. Under appropriate conditions, the stem loop motif results in the presence of a pair of stem loop structures within the double stranded section of the closed linear DNA, such as the molecule schematically depicted in FIG. 9B. The closed linear DNA template may include additional protelomerase recognition sequences, as defined previously.

The DNA template as defined above may be provided in an amount sufficient for use in the process of the invention by any method known in the art. For example, the template may be produced by PCR, template extension or any synthetic means of making DNA.

Amplification and Processing

According to the present invention, there is provided a method of producing closed linear DNA from a closed linear DNA template. Said template may be defined as previously described herein.

According to a first aspect, the present invention relates to an in vitro, cell-free method of producing closed linear DNA molecules comprising:

(a) contacting a template comprising linear, double stranded DNA molecule covalently closed at each end by a portion of a first and a second protelomerase recognition sequence and comprising at least one stem loop motif with a strand-displacing polymerase under conditions promoting amplification of said template in the presence of at least one primer which is capable of binding specifically to a sequence within said stem loop motif;

(b) contacting the DNA produced in (a) with at least one protelomerase under conditions promoting production of closed linear DNA.

The DNA template may optionally comprise further protelomerase recognition sequences, additional to the first and second sequences. Preferably, these additional protelomerase recognition sequences are distinct to and separate from the at least one stem loop motif. The additional protelomerase recognition sequences may be separated from one or both of the closed ends of the closed linear DNA by the at least one stem loop motif. These may be identified as the third, fourth etc. protelomerase recognition sequences.

Optionally, each of the protelomerase recognition sequences or portions thereof may be the same sequence or different sequences, each independent of the other. Different recognition sequences will be acted upon by different protelomerase enzymes, and therefore the appropriate protelomerase enzymes will be required for the production of closed linear DNA.

The DNA template is contacted with at least one strand-displacing polymerase. One, two, three, four or five different strand-displacing polymerases may be used. The strand-displacing type polymerase may be any suitable polymerase, such that it synthesises polymers of DNA.

A polymerase may be highly stable, such that its activity is not substantially reduced by prolonged incubation under process conditions. Therefore, the enzyme preferably has a long half-life under a range of process conditions including but not limited to temperature and pH. It is also preferred that a polymerase has one or more characteristics suitable for a manufacturing process. The polymerase preferably has high fidelity, for example through having proofreading activity. Furthermore, it is preferred that a polymerase displays high processivity, high strand-displacement activity and a low Km for dNTPs and DNA. It is preferred that a polymerase does not display DNA exonuclease activity that is not related to its proofreading activity.

The skilled person can determine whether or not a given polymerase displays characteristics as defined above by comparison with the properties displayed by commercially available polymerases, e.g. Phi29 (New England Biolabs, Inc., Ipswich, MA, US), Deep Vent® (New England Biolabs, Inc.) and *Bacillus stearothermophilus* (Bst) DNA polymerase I (New England Biolabs, Inc.). Where a high processivity is referred to, this typically denotes the average number of nucleotides added by a polymerase enzyme per association/dissociation with the template, i.e. the length of primer extension obtained from a single association event.

Preferred strand displacement-type polymerases are Phi 29, Deep Vent and Bst DNA polymerase I or variants of any thereof. "Strand displacement" describes the ability of a polymerase to displace complementary strands on encountering a region of double stranded DNA during synthesis. The template is thus amplified by displacing complementary strands and synthesizing a new complementary strand. Thus, during strand displacement replication, a newly replicated strand will be displaced to make way for the polymerase to replicate a further complementary strand. The amplification reaction initiates when a primer or the 3' free end of a single stranded template anneals to a complementary sequence on a template (both are priming events). When DNA synthesis proceeds and if it encounters a further primer or other strand annealed to the template, the polymerase displaces this and continues its strand elongation. The strand displacement generates newly synthesised single strands of DNA which can act as a template for more priming events. The priming of the newly synthesised DNA leads to hyper-branching, and a high yield of products. It should be understood that strand displacement amplification methods differ from PCR-based methods in that cycles of denaturation are not essential for efficient DNA amplification, as double-stranded DNA is not an obstacle to continued synthesis of new DNA strands. Strand displacement amplification may only require one initial round of heating, to denature the initial template if it is double stranded, to allow the primer to anneal to the primer binding site if used. Following this, the amplification may be described as isothermal, since no further heating or cooling is required. In contrast, PCR methods require cycles of denaturation (i.e. elevating temperature to 94 degrees centigrade or above) during the amplification process to melt double-stranded DNA and provide new single stranded templates. During strand displacement, the polymerase will displace strands of already synthesised DNA. Further, it will use newly synthesised DNA as a template, ensuring rapid amplification of DNA.

A strand displacement polymerase used in the process of the invention preferably has a processivity of at least 20 kb, more preferably, at least 30 kb, at least 50 kb, or at least 70 kb or greater. In one embodiment, the strand displacement DNA polymerase has a processivity that is comparable to, or greater than phi29 DNA polymerase.

Strand displacement replication occurs during the process of the invention. During strand displacement replication, the template is amplified by displacing already replicated strands, which have been synthesised by the action of the polymerase, in turn displacing another strand, which can be the original complementary strand of a double stranded template, or a newly synthesised complementary strand, the latter synthesised by the action of a polymerase on an earlier primer annealed to the template. Thus, the amplification of the template may occur by displacement of replicated strands through strand displacement replication of another strand. This process may be described as strand displacement amplification or strand displacement replication.

A preferred strand displacement replication process is rolling circle amplification/replication (RCA). The term RCA describes the ability of RCA-type polymerases to continuously progress around a circular DNA template strand whilst extending a hybridised primer. A closed linear DNA template can be denatured to form a single stranded circular DNA. Amplification from such a circle leads to formation of linear products which are single strands of DNA with multiple repeats of amplified DNA linked in series. Further replication from these strands directly may result in hyperbranching. The sequence of the DNA template (a single unit) is multiply repeated within a linear product. Each of these multiple repeat units are identical, and are linked in a series. The initial product of strand displacement amplification from a closed linear DNA is a concatameric single strand of DNA, which is considered to be in the opposite polarity to the original polarity of the closed linear DNA template. However, since each closed linear template includes both the plus and minus strands side by side, the concatameric single strand of DNA produced via amplification includes alternate minus and plus strand sequences in each individual unit. These linear single strands of DNA produced can serve as the basis for multiple hybridisation, primer extension and strand displacement events, resulting in formation of concatameric double stranded DNA products (2 separate complementary strands), again comprising multiple repeats of the individual units (templates) amplified by the polymerase. There are thus multiple copies of each amplified “single unit” DNA in the concatameric double stranded DNA products. RCA polymerases are particularly preferred for use in the process of the present invention. The products of RCA-type strand displacement replication processes may require processing to release single unit DNAs. This is desirable if single units of DNA are required.

In order to allow for amplification, the DNA template is also contacted with one or more primers. The primers are specific for one or more sequences comprised within the DNA template, notably the primer binding site situated in the central section (or loop) of the stem loop motif. The primers are thus specific, meaning that they have a sequence which is complementary to the primer binding site. Complementarity is as defined previously. A single specific primer may be used in the method of the invention due to the complementary nature of the closed linear DNA template. This means that each template comprises both a forward (sense) and reverse (antisense) sequence for the stem loop motif, ensuring that the DNA product produced will also have a reverse (antisense) and a forward (sense) version of the stem loop motif. As mentioned previously, the correct orientation could be in either the sense or the antisense version of the stem loop motif sequence.

Primers may be unlabelled, or may comprise one or more labels, for example radionuclides or fluorescent dyes. Primers may also comprise chemical modifications, typically such that the primer has improved resistance to hydrolysis. For example the primer may preferably comprise one or more phosphorothioate linkages. The primer may be any suitable oligonucleotide, including a DNA primer, ribonucleic acid (RNA) primer or locked nucleic acid (LNA) primer, or any suitable hybrid thereof. Primer lengths/sequences may typically be selected based on temperature considerations i.e. as being able to bind to the template at the temperature used in the amplification step. Analogously, the primer binding site is designed with these considerations in mind.

Additionally, the primer can be synthesized in situ using a primase enzyme. In this version, a primase enzyme can be supplied to build a primer at the open central section of the stem loop motif. Thus, it is also possible to indirectly supply a primer to the template and polymerase.

The contacting of the DNA template with the polymerase and one or more primers may take place under conditions promoting annealing of primers to the DNA template. The conditions include the presence of single-stranded DNA allowing for hybridisation of the primers. The conditions also include a temperature and buffer allowing for annealing of the primer to the template. Appropriate annealing/hybridisation conditions may be selected depending on the nature of the primer. An example of preferred annealing conditions used in the present invention include a buffer, 30 mM Tris-HCl pH 7.5, 20 mM KCl, 8 mM $MgCl_2$. The annealing may be carried out following denaturation using heat by gradual cooling to the desired reaction temperature. Alternative denaturation events include the use of specific concentrations of ions.

Typically, a primer of the invention binds or specifically binds to only the primer binding site within the closed linear DNA template. Primer lengths may vary from, for example, 12, 15, 18, 20 or 30 residues in length. A primer may be of 6 to 30, 12 to 30, 18 to 30 or 25 to 30 residues in length.

Routine methods of primer design and manufacture may be applied to the production of a primer capable of specifically binding to any included primer binding site. Primer lengths/sequences may typically be selected based on temperature considerations such as being able to bind to the template at the temperature used in the amplification step.

Optimally, a primer of the invention binds efficiently to the DNA template following its denaturation to separate the complementary sequences. Denaturation in standard amplification methods typically involves a high temperature "melting" step. Thus a primer can be defined by its melting temperature, or Tm, which is the temperature at which a double-stranded nucleotide separates into single strands. Alternative methods of denaturation may however be used, and these are as discussed below.

Once the primer has annealed or bound to the primer binding site, it is available to start amplification of the DNA template. The primer annealed to the template is incubated under conditions promoting amplification of said template by displacement of replicated strands through strand displacement replication of another strand. The conditions comprise use of any temperature allowing for amplification of DNA, commonly in the range of 20 to 90 degrees centigrade. A preferred temperature range may be about 20 to about 40 or about 25 to about 35 degrees centigrade.

Typically, an appropriate temperature is selected based on the temperature at which a specific polymerase has optimal activity. This information is commonly available and forms part of the general knowledge of the skilled person. For example, where phi29 DNA polymerase is used, a suitable temperature range would be about 25 to about 35 degrees centigrade, preferably about 30 degrees centigrade. The skilled person would routinely be able to identify a suitable temperature for efficient amplification according to the process of the invention. For example, the process could be carried out at a range of temperatures, and yields of amplified DNA could be monitored to identify an optimal temperature range for a given polymerase. The amplification may be carried out at a constant temperature, and it is preferred that the process is isothermal. Since strand displacement amplification is preferred there is no requirement to alter the temperature to separate DNA strands. Thus, the process may be an isothermal process.

Typically, in order to synthesise DNA, the polymerase requires a supply of nucleotides. A nucleotide is a monomer, or single unit, of nucleic acids, and nucleotides are composed of a nitrogenous base, a five-carbon sugar (ribose or deoxyribose), and at least one phosphate group. Any suitable nucleotide may be used. The nitrogenous base may be adenine (A), guanine (G), thymine (T), cytosine (C), and uracil (U). The nitrogenous base may also be modified bases, such as 5-methylcytosine (m5C), pseudouridine (hi), dihydrouridine (D), inosine (I), and 7-methylguanosine (m7G).

It is preferred that the five-carbon sugar is a deoxyribose, such that the nucleotide is a deoxynucleotide. The nucleotide may be in the form of deoxynucleoside triphosphate, denoted dNTP. This is a preferred embodiment of the present invention. Suitable dNTPs may include dATP (deoxyadenosine triphosphate), dGTP (deoxyguanosine triphosphate), dTTP (deoxythymidine triphosphate), dUTP (deoxyuridine triphosphate), dCTP (deoxycytidine triphosphate), dITP (deoxyinosine triphosphate), dXTP (deoxyxanthosine triphosphate), and derivatives and modified versions thereof. It is preferred that the dNTPs comprise one or more of dATP, dGTP, dTTP or dCTP, or modified versions or derivatives thereof. It is preferred to use a mixture of dATP, dGTP, dTTP and dCTP or modified version thereof.

Other conditions promoting amplification of the closed linear DNA template comprise the presence of metal ions, suitable buffering agents/pH and other factors which are required for enzyme performance or stability. Suitable conditions include any conditions used to provide for activity of polymerase enzymes known in the art.

For example, the pH of the reaction mixture may be within the range of 3 to 12, preferably 5 to 9 or about 7, such as about 7.9. pH may be maintained in this range by use of one or more buffering agents. Such buffers include, but are not restricted to MES, Bis-Tris, ADA, ACES, PIPES, MOBS, MOPS, MOPSO, Bis-Tris Propane, BES, TES, HEPES, DIPSO, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, CABS, phosphate, citric acid-sodium hydrogen phosphate, citric acid-sodium citrate, sodium acetate-acetic acid, imidazole and sodium carbonate-sodium bicarbonate.

While the application of heat (exposure to 95° C. for several minutes) is used to denature double stranded DNA other approaches may be used which are more suitable for DNA synthesis. Double stranded DNA can be readily denatured by exposure to a high or low pH environment or where cations are absent or present in very low concentrations, such as in deionised water. The polymerase requires the binding of a short oligonucleotide primer sequence to a single stranded region of the DNA template to initiate its replication. The stability of this interaction and therefore the efficiency of DNA amplification may particularly be influenced by the concentration of metal cations and particularly divalent cations such as $Mg^{2+}$ ions which may be seen as an integral part of the process.

The amplification conditions may also comprise metal ions. The reaction mixture may also comprise salts of metals such as, but not limited to, salts of divalent metal ions: magnesium ($Mg^{2+}$), manganese ($Mn^{2+}$), calcium ($Ca^{2+}$), beryllium ($Be^{2+}$), zinc ($Zn^{2+}$) and strontium ($Sr^{2+}$), or salts of monovalent metal ions, including but not limited to lithium ($Li^{+}$), sodium ($Na^{+}$) or potassium ($K^{+}$). The salts may include chlorides, acetates and sulphates. Other salts that may be included are ammonium salts, in particular ammonium sulphate.

Detergents may also be included in the amplification conditions. Examples of suitable detergents include Triton X-100, Tween 20 and derivatives of either thereof. Stabilising agents may also be included in the reaction mixture. Any suitable stabilising agent may be used, in particular, bovine serum albumin (BSA) and other stabilising proteins. Reaction conditions may also be improved by adding agents that relax DNA and make template denaturation easier. Such agents include, for example, dimethyl sulphoxide (DMSO), formamide, glycerol and betaine. DNA condensing agents may also be included in the reaction mixture. Such agents include, for example, polyethylene glycol or cationic lipid or cationic polymers.

It should be understood that the skilled person is able to modify and optimise amplification and incubation conditions for the process of the invention using these additional components and conditions on the basis of their general knowledge. Likewise the specific concentrations of particular agents may be selected on the basis of previous examples in the art and further optimised on the basis of general knowledge. As an example, the amount of polymerase present in the reaction mixture may be optimised. This may involve making further addition of polymerase enzyme to the reaction mixture during the DNA synthesis. As a further example, the amount of DNA template may be optimised. This may involve making further addition of DNA template to the reaction mixture during DNA synthesis.

As an example, a suitable reaction buffer used in rolling circle amplification-based methods in the art is 50 mM Tris HCl, pH 7.5, 10 mM $MgCl_2$, 20 mM $(NH_4)_2SO_4$, 5% glycerol, 0.2 mM BSA, 1 mM dNTPs. A preferred reaction buffer used in the RCA amplification of the invention is 30 mM Tris-HCl pH 7.4, 30 mM KCl, 7.5 mM $MgCl_2$, 10 mM $(NH_4)_2SO_4$, 4 mM DTT, 2 mM dNTPs. This buffer is particularly suitable for use with Phi29 RCA polymerase.

The amplification conditions may also comprise use of one or more additional proteins. The DNA template may be amplified in the presence of at least one pyrophosphatase, such as Yeast Inorganic pyrophosphatase. Two, three, four, five or more different pyrophosphatases may be used. These enzymes are able to degrade pyrophosphate generated by the polymerase from dNTPs during strand replication. Build-up of pyrophosphate in the reaction can cause inhibition of DNA polymerases and reduce speed and efficiency of DNA amplification. Pyrophosphatases can break down pyrophosphate into non-inhibitory phosphate. An example of a suitable pyrophosphatase for use in the process of the present invention is Saccharomyces cerevisiae pyrophosphatase, available commercially from New England Biolabs, Inc.

Any single-stranded binding protein (SSBP) may be used in the process of the invention, to stabilise single-stranded DNA. SSBPs are essential components of living cells and participate in all processes that involve ssDNA, such as DNA replication, repair and recombination. In these processes, SSBPs bind to transiently formed ssDNA and may help stabilise ssDNA structure. An example of a suitable SSBP for use in the process of the present invention is T4 gene 32 protein, available commercially from New England Biolabs, Inc.

Acting upon the primer bound to the template, the polymerase acts to produce multiple repeated and identical units of said DNA template linked in series, otherwise described as a concatameric single strand of DNA. This concatamer comprises multiple identical repeats of the template linked in series. The strand may extend to 100 kb. This concatamer is a single strand, but it will be appreciated that the concatamer may well form secondary structures via intra-strand base pairing, forming sections of duplexed sequence. Given that the preferred template (closed linear DNA) includes side-by-side complementary sequences, the formation of intra-strand base pairs is likely. These complementary sequences within the same strand may anneal to one another, forming duplexes of sequence. However, the stem loop motif prevents the internal base pairing of the loop or central section. It is under the conditions used for amplification as defined herein that it is preferred that the sequence of the stem loop motif forms the secondary structure permitting looping out of the central section as single stranded DNA, preventing this sequence from base pairing to internal complementary sequences. This concatamer with stem loop structures allows for the further replication of the template, since it allows for the one or more primers to anneal to the initial product of amplification, and enables a complementary strand of DNA to be synthesised. The single strand of concatameric DNA may still form a DNA nanoflower, but retains single stranded sequences within the loops. These loops thus provide a suitable structure or site within which to place a primer binding site, allowing for DNA polymerase to use the single strand of concatameric DNA as a template. It is central to the method of the invention that concatamers which are comprised of two distinct complementary strands of DNA are produced, since this is the final intermediate product before closed linear DNA is produced.

The concatameric single strand of DNA with stem loop structures forms a third aspect of the invention. Thus, the invention also provides a concatameric single strand of DNA comprising two or more identical units of DNA sequence covalently linked together in a series, each unit comprising at least one portion of a protelomerase recognition sequence and at least one stem loop structure.

The concatameric single strand of DNA as described herein may comprise multiple repeat units, each unit being the sequence for a linear double stranded DNA as defined herein. Each unit may thus comprise two portions of a protelomerase recognition sequence (which may be the same or different sequences) and at least one stem loop motif to form a stem loop structure. If additional protelomerase recognition sequences are present in the template, these will also be present in the concatameric single strand of DNA in each unit, as set out in the template. It is preferred that the single stranded concatamer will include a stem loop motif flanked on either side by a portion of a protelomerase recognition sequence. It will be understood that each protelomerase recognition sequence is present as a portion as the concatamer is single stranded. In one embodiment, the stem loop motif is flanked by portions of protelomerase recognition sequences that are different. It will be understood that these flanking sequences may indeed be separated by spacer sequences of any appropriate length.

It is preferred that the stem loop structure formed is within the stem loop motif from the template closed linear DNA, as previously defined. Optionally, the stem loop structure may be formed by the complementary flanking sequences annealing to form a stem structure. The central section then loops out between the ends of the stem as a single stranded DNA. It is preferred that the stem loop structure includes a primer binding site, optionally in the central section. The loop structure is critical, since it maintains a portion of sequence in single stranded format and prevents the primer binding site forming inter-strand base pairs with its complementary sequence within the single strand of concatameric DNA. Thus, the primer binding site within the loop or central section is kept open and free for primer binding.

The stem loop structure predominates as a result of amplification of a stem loop motif containing closed linear DNA template since it is formed before its reverse complementary sequence is synthesized. This can be enhanced by carefully selecting the sequence of the residues in the stem to ensure strong base pairing is present. Those skilled in the art are aware of techniques for ensuring the presence of particular secondary structures in single stranded DNA. The design of such sequences is as discussed previously for the template itself.

The presence of the single stranded loop within the concatameric single strand of DNA, (which strand is produced by the action of the polymerase on the template) allows the one or more primers to anneal to the primer binding site and permits the generation of a complementary DNA strand to the initial strand and thus a DNA concatamer with two distinct complementary strands (double stranded concatameric DNA). Either strand could then be used as a further template or double stranded concatameric DNA could be used as a substrate for the one or more protelomerase enzymes.

It is preferred that the amplification step is performed under conditions which promote the formation of a stem loop structure within the concatameric single strand of DNA. Such conditions may simply be those that are optimised for amplification, since these tend to favour the maintenance of single-stranded structure. Under such conditions, stem loops structures that are derived from the stem loop motif including complementary flanking regions form due to base pairing. Alternatively, these conditions may include the addition of one or more agents that promote the formation of loop structures within the single stranded DNA concatamer. This includes the addition of bridging oligonucleotides. These are short (1 to 100, preferably 1 to 90, 1 to 80, 1 to 70, 1 to 60, 1 to 50, 1 to 40, 1 to 30, 1 to 20 or 1 to 10 residues in length) oligonucleotides that are complementary in sequence to the flanking regions within the sequence of the stem loop motif. Ideally, the bridging oligonucleotide is formed of two parts, the first that is complementary to the first flanking sequence, and the second which is complementary to the second flanking sequence. Optionally, there is no gap between these two parts, but in an alternative embodiment, they are separated by 1-50 residues, or alternatively 1 to 40, 1 to 30, 1 to 20, 1 to 10 or 1 to 5 residues. The bridging oligonucleotide can therefore bring the two flanking sequences of the stem loop motif together or nearly so, forcing the central section out into a single stranded loop. Complementarity is as defined previously.

The bridging oligonucleotide may be any suitable nucleic acid. It is preferred that the bridging oligonucleotide is non-extensible by the DNA polymerase, for example, it includes modified residues which prevent extension. Optionally, the bridging oligonucleotide comprises a type of nucleic acid that anneals more strongly to DNA than DNA itself, for example a locked nucleic acid (LNA) or an RNA.

Those skilled in the art are capable of utilising complementarity between residues to design appropriate nucleotides and oligonucleotides for use in the present invention. Thus, it will be routine to design various primer binding site and primer pairs, using this to design a sequence for a stem loop motif or stem loop structure. Further bridging oligonucleotides and flanking sequences can be appropriately designed. Those skilled in the art will be aware routine textbooks such as Molecular Biology of the Gene, 7th Edition, Watson et al, 2014, hereby incorporated by reference.

In addition to the amplification step, a process of the invention for amplification of closed linear DNA also comprises a processing step for production of closed linear DNA. Amplified DNA is contacted with at least one protelomerase under conditions promoting production of closed linear DNA. This simple processing step based on protelomerase is advantageous over other methods used for production of closed linear DNA molecules. The amplification and processing steps can be carried out simultaneously or concurrently. However, preferably, the amplification and processing steps are carried out sequentially with the processing step being carried out subsequent to the amplification step (i.e. on amplified DNA).

A protelomerase is any polypeptide capable of cleaving and re-joining a template comprising a protelomerase recognition sequence in order to produce a covalently closed linear DNA molecule. Thus, the protelomerase has DNA cleavage and ligation functions. Enzymes having protelomerase-type activity have also been described as telomere resolvases (for example in *Borrelia burgdorferi*). A typical substrate for protelomerase is circular double stranded DNA. If this DNA contains a complete protelomerase recognition sequence, the enzyme can cut the DNA at this sequence and ligate the ends to create a linear double stranded covalently closed DNA molecule. The requirements for protelomerase recognition sequences are discussed above. As also outlined above, the ability of a given polypeptide to catalyse the production of closed linear DNA from a template comprising a protelomerase recognition sequence can be determined using any suitable assay described in the art.

The production of closed linear DNA may require the use of at least one protelomerase. The process of the invention may comprise use of more than one protelomerase, such as two different protelomerases, one for each end of the closed linear DNA molecule. If additional protelomerase recognition sequences are used within the DNA template, then more protelomerase enzymes will be required for processing, and the skilled person can make an appropriate selection, depending on the required result. Variations of the process and various potential products are depicted in FIGS. 14 and 15. Processing can take place from double-stranded duplexes or single stranded concatamers folded into nanoflowers.

Examples of suitable protelomerases include those from bacteriophages such as phiHAP-1 from *Halomonas aquamarina* (SEQ ID NO: land 2), PY54 from *Yersinia enterocolytica* (SEQ ID NO: 3 and 4), phiK02 from *Klebsiella oxytoca* (SEQ ID NO: 5 and 6), VP882 from *Vibrio* sp. (SEQ ID NO: 7 and 8), Vp58.5 from *Vibrio parahaemolyticus* (SEQ ID NO: 13 and 14) and N15 from *Escherichia coli* (SEQ ID NO: 9 and 10), or variants of any thereof. Use of bacteriophage N15 protelomerase or a variant thereof is particularly preferred. This enzyme is also referred to as TelN. These enzymes are further described in WO2012/017210, incorporated herein by reference.

The processes of the present invention may be performed with a closed linear DNA template that comprises portions of protelomerase recognition sequence only at the closed ends of the template. In this instance, a cognate protelomerase for each end will be required to convert the double stranded concatameric DNA produced using the methods of the invention into closed linear DNA products. In some instances, the same protelomerase will be sufficient for this task, since each end is a portion of the same protelomerase recognition sequence.

In an alternative embodiment, the process of the invention may be performed with a closed linear DNA template that not only has portions of protelomerase recognition sequences capping the ends of the template (first and second sequences), but also has additional protelomerase recognition sequences. (such as third and fourth sequences). As previously discussed, it is preferred that at least two additional protelomerase recognition sequences are included in the DNA template. These are preferably separated in the closed linear DNA template from the capped ends of the template by at least one stem loop motif. Thus, an exemplary closed linear DNA template may have the sequence (see also FIG. 12):

CAP1-STEM LOOP1-PTS 3-SEQUENCE-PTS4-STEM LOOP2-CAP2

Wherein the CAP1 is a portion of a first protelomerase sequence;

The first and second stem loop motifs are the same or different;

PTS3 and PTS4 are the third and fourth protelomerase recognition sequences which are the same or different;

CAP2 is a portion of a second protelomerase sequence; and

SEQUENCE is the target sequence for inclusion into a closed linear DNA product.

Protelomerase recognition sequences 1 and 2 may be the same or different, but are preferably different to protelomerase recognition sequences 3 and 4.

These sequences may be adjacent to each other, near to each other or separated by intervening sequences.

The single stranded DNA concatamer that results from the amplification of a closed linear DNA template with additional protelomerase recognition sequences may also form DNA nanoflowers. This is depicted in FIG. 15, along with the method to process these nanoflowers.

Thus DNA nanoflowers produced by amplification of a template with additional protelomerase recognition sequences, will also contain these sequences. The present inventors have devised a method that allows the direct release of closed linear DNA products from the single stranded DNA concatamer, which has preferably formed intra-strand base pairs and duplexes, and folded into a nanoflower. This method does not rely upon the formation of a separate complementary strand of DNA to form a DNA duplex prior to processing, and it is therefore not necessary to try to re-prime a folded single strand of DNA. Thus, if additional protelomerase recognition sequences are included in the template, these are replicated in the folded single stranded concatamer, and a whole duplex protelomerase recognition sequence is present as a target for a protelomerase. In this instance, it is possible to contact the amplified DNA with a cognate protelomerase for the additional protelomerase recognition sequences, and liberate a closed linear DNA. The by-products of such a process is a mini closed linear DNA with a stem loop motif contained in the linear DNA section (see FIG. 15).

Such a method to liberate closed linear DNA from the DNA nanoflowers is attractive, because it allows for a "clean-up" of any nanoflowers that are left at the end of the reaction, in case reaction components such as primers, polymerase or nucleotides have been exhausted. It also allows for the production of a closed linear DNA molecule with only the target sequence present, with the removal of the stem loop motif, which may be undesirable for certain indications. Moreover, the additional protelomerase sequences may be used to process double-stranded concatamers as depicted in FIG. 14, this releasing the same product, but with different by-products.

The inventors envisage that the method of the invention may be performed such that closed linear DNA is produced from both double stranded DNA concatamers and single stranded DNA concatamers, both of which have been amplified from a closed linear DNA template, and thus a combination of FIGS. 14 and 15 will operate in practice, depending on the template and enzyme selection. It allows for a selection of the desired product by varying which protelomerase enzyme is added to the amplified DNA, and thus alters which product is obtained. The skilled person will appreciate that a selection can be made simply to add the protelomerase enzyme(s) for the first and second protelomerase recognition sequences that form the caps of the template, and/or to add the protelomerase enzyme(s) for the additional (for example, third and fourth) protelomerase recognition sequences that form part of the duplex section of the closed linear DNA.

The DNA amplified from the DNA template is thus preferably incubated with at least one protelomerase under conditions promoting production of closed linear DNA. In other words, the conditions promote the cleavage and re-ligation of a duplex DNA comprising a protelomerase recognition sequence to form a covalently closed linear DNA with hairpin ends. Conditions promoting production of closed linear DNA comprise use of any temperature allowing for production of closed linear DNA, commonly in the range of 20 to 90 degrees centigrade. The temperature may preferably be in a range of 25 to 40 degrees centigrade, such as about 25 to about 35 degrees centigrade, or about 30 degrees centigrade. Appropriate temperatures for a specific protelomerase may be selected according to the principles outlined above in relation to temperature conditions for DNA polymerases. A suitable temperature for use with *E. coli* bacteriophage TelN protelomerase of SEQ ID NO: 15 is about 25 to about 35 degrees centigrade, such as about 30 degrees centigrade. Conditions promoting the production of closed linear DNA also include the presence of double stranded DNA concatamers, with both portions of the protelomerase recognition sequence forming a complete site upon which the protelomerase may act.

Conditions promoting production of closed linear DNA also comprise the presence of a protelomerase and suitable buffering agents/pH and other factors which are required for enzyme performance or stability. Suitable conditions include any conditions used to provide for activity of protelomerase enzymes known in the art. For example, where *E. coli* bacteriophage TelN protelomerase is used, a suitable buffer may be 20 mM Tris HCl, pH 7.6; 5 mM $CaCl_2$; 50 mM potassium glutamate; 0.1 mM EDTA; 1 mM dithiothreitol (DTT). Agents and conditions to maintain optimal activity and stability may also be selected from those listed for DNA polymerases.

In some embodiments, it may be possible to use the same conditions for activity of protelomerase as are used for DNA amplification and/or stem loop structure formation. In particular, use of the same conditions is described where DNA amplification and processing by protelomerase are carried out simultaneously or concurrently. In other embodiments, it may be necessary to change reaction conditions where conditions used to provide optimal DNA polymerase activity lead to sub-optimal protelomerase activity. Removal of specific agents and change in reaction conditions may be achievable by filtration, dialysis and other methods known in the art. The skilled person would readily be able to identify conditions allowing for optimal DNA polymerase activity and/or protelomerase activity.

In a particularly preferred embodiment, for use in amplification of DNA by a strand-displacing polymerase, preferably phi29, the DNA amplification is carried out under buffer conditions substantially identical to or consisting essentially of 35 mM Tris-HCl, 50 mM KC1, 14 mM $MgCl_2$, 10 mM $(NH_4)_2$ $SO_4$, 4 mM DTT, 1 mM dNTP at a temperature of 25 to 35 degrees centigrade, such as about 30 degrees centigrade. The processing step with protelomerase may then preferably be carried out with TelN, and/or preferably under buffer conditions substantially identical to or consisting essentially of 20 mM Tris HCl, pH 7.6; 5 mM $CaCl_2$; 50 mM potassium glutamate; 0.1 mM EDTA; 1 mM dithiothreitol (DTT) at a temperature of 25 to 35 degrees centigrade, such as about 30 degrees centigrade.

Following production of closed linear DNA by the action of protelomerase, the process of the invention for amplification of closed linear DNA may further comprise a step of purifying the linear covalently closed DNA product. Similarly, DNA amplified according to other processes of the invention may also be purified. The purification referred to above will typically be performed to remove any undesired products. Purification may be carried out by any suitable means known in the art. For example, processing of amplified DNA or linear covalently closed DNA may comprise phenol/chloroform nucleic acid purification or the use of a column which selectively binds nucleic acid, such as those commercially available from Qiagen. The skilled person can routinely identify suitable purification techniques for use in isolation of amplified DNA.

The invention further relates to a kit suitable for performing the method of any aspect or embodiment, said kit comprising:

(a) a linear, double stranded DNA molecule covalently closed at each end by a portion of a protelomerase recognition sequence, wherein the sequence of said linear, double stranded DNA molecule includes at least one stem loop motif;

(b) one or more protelomerase enzymes; and optionally;

(c) a bridging oligonucleotide.

The kit may contain a template closed linear DNA as hereinbefore described, including those with additional protelomerase recognition sequences.

The kit may further comprise one or more of the following components: a DNA polymerase, a primer, appropriate buffers, nucleotides, metal cations, pyrophosphatase and/or nucleases. The linear, double stranded DNA molecule can be any such molecule as described herein.

Sequences of the Invention:

*Halomonas* phage phiHAP-1 protelomerase nucleic acid sequence (SEQ ID NO:1)

*Halomonas* phage phiHAP-1 protelomerase amino acid sequence (SEQ ID NO: 2)

*Yersinia* phage PY54 protelomerase nucleic acid sequence (SEQ ID NO: 3)

*Yersinia* phage PY54 protelomerase amino acid sequence (SEQ ID NO: 4)

*Klebsiella* phage phiKO2 protelomerase nucleic acid sequence (SEQ ID NO.:5)

*Klebsiella* phage phiKO2 protelomerase amino acid sequence (SEQ ID NO: 6)

Vibriophage VP882 protelomerase nucleic acid sequence (SEQ ID NO: 7)

Vibriophage VP882 protelomerase amino acid sequence (SEQ ID NO: 8)

*Escherichia coli* bacteriophage N15 telomerase (TelN) and Secondary immunity repressor (cA) nucleic acid sequence (SEQ ID NO: 9)

*Escherichia coli* bacteriophage N15 telomerase amino acid sequence (SEQ ID NO: 10)

Protelomerase TelA from *Agrobacterium tumefaciens* Strain C58 Native Gene Sequence TelA (1329 bp) (SEQ ID NO: 11)

TelA Protein Sequence (SEQ ID NO: 12) Gp40 VP58.5 nucleotide sequence (SEQ ID NO: 13)

*Vibrio*: gp40 protein [*Vibrio* phage VP58.5] amino acid (SEQ ID NO 14)

*Escherichia coli* phage N15 protelomerase recognition sequence (SEQ ID NO 15)

*Klebsiella* phage phiK02 protelomerase recognition sequence (SEQ ID NO 16)

*Yersinia enterolytica* phage PY54 protelomerase recognition sequence (SEQ ID NO 17)

*Vibrio* sp. phage VP882 protelomerase recognition sequence (SEQ ID NO 18)

*Borrelia burgdorferi* protelomerase recognition sequence (SEQ ID NO 19)

*Agrobacterium tumefaciens* strain C58 protelomerase recognition sequence (SEQ ID NO 20)

GP40 VP58.5 recognition sequence: (SEQ ID NO 21)

*Agrobacterium tumefaciens* strain C58 protelomerase core recognition sequence (SEQ ID NO 22):

Stem-loop sequences: in the format of nucleotide length of each part: stem, spacer, primer binding site, spacer, stem (i.e. for SEQ ID 25, the stem is 25 base pairs in length and there is no spacer to the 15 bases forming the primer binding site):

SEQ ID 23:25-0-15-0-25

SEQ ID NO. 24: 25-5-15-5-25

SEQ ID NO. 25: 25-10-15-0-25

SEQ ID NO. 26:25-0-15-10-25

SEQ ID NO 27: 15-0-15-0-15

SEQ ID NO. 28:15-5-15-5-15

SEQ ID NO. 29:15-10-15-0-15

SEQ ID NO 30: 15-0-15-10-15

SEQ ID NO 31: FIG. 10*a* stem loop

SEQ ID NO:32: 4 to 11 primer FIG. 10*a*

SEQ ID NO:33: 3 to 12 primer FIG. 10*a*

SEQ ID NO:34: 2 to 13 primer FIG. 10*a*

SEQ ID NO:35: 1 to 14 primer FIG. 10*a*

SEQ ID NO:36: 0 to 15 primer FIG. 10*a*

SEQ ID NO: 37: NO-11/short1 primer

The invention will now be described with reference to several non-limiting examples:

EXAMPLES

Materials and Methods

Qubit™ fluorometer—Uses fluorescent dyes to detect single stranded (SS)/double stranded (ds)DNA, RNA or protein in a sample. Used in the broad-range dsDNA assay mode, it gives an accurate quantification of dsDNA in a sample without interference from ssDNA such as primers or dNTPs Polyethylene glycol 8000 (PEG8000)—ThermoFisher Scientific, Water-Sigma Aldrich, nuclease-free, deionised and sterilised (molecular biology grade) dNTPs (lithium salt)—Bioline, stock concentration 100 mM, Primers various—Oligofactory, TelN-Enzymatics, Φ29 DNA-Enzymatics, XbaI-NEB, ApaLI-NEB, T5 exonuclease-NEB, Exonuclease III-Enzymatics, Pyrophosphatase-Enzymatics, Proteinase K-Sigma Aldrich, 10×TLG buffer composition: 300 mM Tris (pH 7.9); 300 mM KCl; 20 mM DTT; 50 mM $(NH_4)_2SO_4$; 75 mM $MgCl_2$—Sigma Aldrich.

Example 1

Production of stem loop closed linear DNA from a plasmid template. Table 1 below shows the conditions under which plasmid proTLx-K B5X4 eGFP 53SL (see FIG. 11) was amplified. RCA reactions were setup at room temperature and reagents added in the order indicated. Reactions were carried out in polypropylene tubes and incubated overnight at 30° C.

TABLE 1

| | Setup conditions for plasmid amplification | | | |
|---|---|---|---|---|
| | Reaction Component | Stock concentration | Reaction concentration | Volume added |
| 1 | Template proTLx-K B5X4 eGFP 53SL (see FIG. 11) | 1000 μg/ml | 2 ng/μl | 10 μl |
| 2 | NaOH | 1M | 5 mM | 25 μl |
| 3 | 10xTLG pH 7.9 buffer (300 mM Tris-HCl), 300 mM KCl, 75 mM $MgCl_2$, 50 mM $(NH_4)_2SO_4$, 20 mM DTT) | 10x | 1x | 500 μl |
| 4 | Water | n/a | n/a | 4200 μl |
| 5 | dNTPs | 100 mM | 4 mM | 200 μl |
| 6 | Phi29 DNA polymerase | 100,000 U/ml | 200 U/ml | 10 μl |
| 7 | N0-11 primer (SEQ ID NO: 37) (primer binding site is within the palindromic sequence of the protelomerase recognition sequence) | 5 mM | 50 μM | 50 μl |
| 8 | Pyrophosphatase | 2 U/ml | 0.0002 U/ml | 0.5 μl |

Raw concatameric products of amplification of the plasmid template were incubated with 3 μM protelomerase TelN at 30° C. for 10 mins. 750U/ml of XbaI (NEB) was then added and DNA was incubated at 37° C. for 3 hrs before addition of 500 U/ml of Exonuclease III (Enzymatics) and incubation for a further 2 hours at 37° C. The reaction was then diluted 2 fold in 500 mM NaCl/100 mM $MgCl_2$ buffer, and 2.5% (w/v) polyethylene glycol 8000 (PEG8000) was added. This was centrifuged at 4,500 g for 10 mins and the supernatant recovered. Following addition of 2.5% PEG8000 (final concentration 5%) to the supernatant and a further centrifugation step, the resulting supernatant was discarded and the pellet washed with 5m1 of 100% ethanol. The DNA was re-pelleted by centrifugation, the ethanol discarded and the DNA re-suspended in water. The stem loop containing closed linear DNA (db_eGFP 53SL) was stored at −20° C. and used for the experiments described below Amplification of Stem Loop Closed Linear DNA Experiments indicate that for closed linear DNA amplification using a single primer that binds in the palindromic protelomerase TelN target sequence, no yield increase is possible with dNTP supplementation (see Table 2). This is due to the formation of highly folded concatameric DNA (nanoflowers) as the single strand rolls off the DNA template. This highly folded structure makes priming and further dNTP incorporation more difficult, preventing conversion of DNA nanoflowers into double stranded concatamers.

TABLE 2

| dsDNA yield results from feeding of a standard closed linear DNA (db_eGFP) amplification | | | |
|---|---|---|---|
| No of 2 mM dNTP feeds | None | 1 | 2 |
| Total [dNTP] | 3.5 mM | 5.5 mM | 7.5 mM |
| [dsDNA] μg/ml | 248 | 270 | 258 |

In order to determine if stem loop priming is beneficial for closed linear DNA amplification, reactions were performed on a dbDNA template with introduced stem loops (db_eGFP 53SL) and primers specific for this region. Table 3 shows the conditions under which stem loop dbDNA amplification was performed.

TABLE 3

| | Setup conditions for stem loop closed linear DNA amplification | | | |
|---|---|---|---|---|
| | Reaction Component | Stock concentration | Reaction concentration | Volume added |
| 1 | Template db_eGFP 53SL | 200 μg/ml | 2 ng/μl | 10 μl |
| 2 | NaOH | 1M | 5 mM | 5 ul |
| 3 | Primer (see FIG. 10a) | 1 mM | 35 μM | 35 μl |
| 4 | 10xTLG pH 7.9 buffer (300 mM Tris-HCl, 300 mM KCl, 75 mM $MgCl_2$, 50 mM $(NH_4)_2SO_4$, 20 mM DTT) | 10x | 1x | 100 μl |
| 5 | Water | n/a | n/a | 825 μl |
| 6 | Phi29 DNA polymerase | 100,000 U/ml | 200 U/ml | 2 μl |
| 7 | dNTPs | 100 mM | 2.5 mM | 25 μl |
| 8 | Pyrophosphatase | 2 U/ml | 0.0002 U/ml | 0.1 μl |

Reactions were setup at room temperature and reagents added in the order indicated followed by incubation at 30° C. overnight. 5 different primers specific for the introduced stem loop were tested (see FIG. 10*b*) in order to determine if priming (and subsequent DNA amplification) in the concatamer stem loops was possible after the initial loop priming in the closed linear DNA template.

Reactions were supplemented with 2.5 mM dNTPs at 16 hrs, 40 hrs, 64 hrs and DNA concentrations determined at 15.5 hrs, 39.5 hrs, 63.5 hrs and 87.5 hrs using the Qubit™ fluorometric quantification according to manufacturer's instructions (values for dsDNA are tabulated in Table 4). 8 μl samples of each reaction was also taken for gel analysis on Day 3 and digested with 10 μM protelomerase TelN. For gel analysis, samples were heated to 75° C. for 2 mins before separation on a 0.8% agarose gel using standard procedures.

Table 3 show the dsDNA reaction yield of amplified closed linear DNA after feeding of reactions with dNTPs. In contrast to a standard closed linear DNA amplification (Table 2), it can be seen that for all primers tested, the yield of dsDNA product increases with dNTP additions. This indicates that the concatameric product produced by amplification of the closed linear DNA template (db_eGFP 53SL) is primable and is further amplified to produce more dsDNA product. FIG. 10B shows that the dsDNA product is converted to a closed linear DNA (db_eGFP 53SL) by treatment with TelN protelomerase. This show that all the primers are specific and are capable of producing the desired closed linear DNA end-product (with included stem loop motif)

TABLE 4 dsDNA yield results from feeding of a stem loop closed linear DNA (db_eGFP) primed with different stem loop specific primers

| No of 2.5 mM dNTP feeds | None | 1 | 2 | 3 |
|---|---|---|---|---|
| Total [dNTP] | 2.5 mM | 5.0 mM | 7.5 mM | 10 mM |
| [dsDNA] μg/ml from 4 to 11 primer | 208 | 356 | 430 | 810 |
| [dsDNA] μg/ml from 3 to 12 primer | 193 | 364 | 430 | 890 |
| [dsDNA] μg/ml from 2 to 13 primer | 382 | 672 | 754 | 2400 |
| [dsDNA] μg/ml from 1 to 14 primer | 382 | 734 | 664 | 4620 |
| [dsDNA] μg/ml from 0 to 15 primer | 300 | 426 | 552 | 2560 |

Example 2

Production of a Closed Linear DNA with Additional Protelomerase Recognition Sequences from a Plasmid Template Table 4 below shows the conditions under which the plasmid proTLx-K B5X4A4 eGFP 15-0-15-10 (see FIG. 17) was amplified. RCA reactions were setup at room temperature and reagents added in the order indicated. Reactions were carried out in polypropylene tubes and incubated overnight at 30° C.

TABLE 5

Setup conditions for plasmid amplification

| | Reaction Component | Stock concentration | Reaction concentration | Volume added |
|---|---|---|---|---|
| 1 | Template proTLx-K B5X4A4 eGFP 15-0-15-10 (see FIG. 17) | 1000 mg/l | 0.5 mg/l | 2.5 μl |
| 2 | NaOH | 1M | 5 mM | 25 μl |
| 3 | 10xTLG pH 7.9 buffer (300 mM Tris-HCl), 300 mM KCl, 75 mM $MgCl_2$, 50 mM $(NH_4)_2SO_4$, 20 mM DTT) | 10x | 1x | 500 μl |
| 4 | Water | n/a | n/a | 4247 μl |
| 5 | dNTPs | 100 mM | 3.5 mM | 175 μl |
| 6 | Phi29 DNA polymerase | 100,000 U/ml | 200 U/ml | 10 μl |
| 7 | 2-13 primer FIG. 10A (2 to 13) | 5 mM | 40 μM | 40 μl |
| 8 | Pyrophosphatase | 2 U/ml | 0.0002 U/ml | 0.5 μl |

Raw concatameric products of amplification of the plasmid template proTLx-K B5X4A4 eGFP 15-0-15-10-15 were incubated with 4 μM protelomerase VP58.5 at 30° C. for 10 mins. 200 U/ml of ApaLI (NEB) was then added and DNA was incubated at 37° C. for 3 hrs before addition of 200 U/ml of Exonuclease III (Enzymatics) and 50 U/ml T5 exonuclease (NEB) and incubation for a further 3 hours at 37° C. 2 μl/ml Proteinase K (Sigma) was added, and the reaction incubated at 37° C. overnight. The reaction was then diluted 2 fold in 500 mM NaCl/100 mM $MgCl_2$ buffer, and 2.5% (w/v) polyethylene glycol 8000 (PEG8000) was added. This was centrifuged at 4,500 g for 10 mins and the supernatant recovered. Following addition of 2.5% PEG8000 (final concentration 5%) to the supernatant and a further centrifugation step, the resulting supernatant was discarded and the pellet washed with 5 ml of 100% ethanol. The DNA was re-pelleted by centrifugation, the ethanol discarded and the DNA re-suspended in water. The closed linear DNA template was stored at −20° C. and used for the experiments described below

Example 3

Amplification of a Closed Linear DNA which Includes Additional Protelomerase Recognition Sequences.

Essentially, the closed linear DNA template used in this example comprises the generic structure illustrated in FIG. 12. The protelomerase A recognition sequence caps the closed linear DNA while a different protelomerase B recognition sequence is present as a complete site within the double stranded section and is capable of being cleaved and ligated by a cognate protelomerase. The two protelomerase recognition sites are in close proximity but separated by a stem loop motif containing an open single stranded region for binding an oligonucleotide primer to initiate amplification of the template. Amplification of this template by a rolling circle, strand displacing DNA polymerase yields two types of concatameric DNA products: single stranded concatamers that because of their internal sequence complementarity, can fold into nanoflowers as depicted in FIG. 15 and double stranded concatamers where the complementary DNA strand is synthesised following priming and amplification from the nanoflower stem loop motifs. This is similar to the standard stem loop closed linear DNA described in Example 1. However, the use of a closed linear DNA with additional protelomerase recognition sequences (FIG. 12) over a standard stem loop closed linear DNA template (FIG. 9B) has a number of advantages. With reference to FIGS. 14 and 15, treatment with protelomerase B will excise a closed linear DNA (capped with portions of a protelomerase B recognition site) from both a single stranded and double stranded concatamer. In standard rolling circle amplification reactions of closed linear DNA, including the stem loop variant described in Example 1, single stranded concatamer that can be produced in significant amounts is normally a waste product. Thus, use of a closed linear DNA template with additional protelomerase recognition sequences allows a more efficient production of a standard closed linear DNA and allows for the removal of the stem loop motif and the first and second protelomerase recognition sequences, which previously formed the closed ends of the template.

In this embodiment, protelomerases A and B can be any protelomerase or other enzyme capable of cutting and ligating DNA as long as they are two distinct enzymes with different recognition sequences. In the experimental data described below, protelomerase A is VP58.5 and protelomerase B is TelN.

Experimental description: Amplification was carried out as for Example 2, with the exception that template concentration was 1 mg/l. The reaction was also processed as above, minus the ApaLI addition and incubation. The reaction was split in half, with one half processed with VP58.5 and the other, TelN substituted.

The products were run on a 0.8% agarose gel to check sizes; FIG. 16 shows the protelomerase digest stage showing expected product and sub-products for TelN (lane B) and VP58.5 (lane A) cleavage and joining, and the exonuclease stage (lanes BX and AX respectively) showing progression of the digestion of "open" side products with closed linear DNA constructs remaining intact. As expected from the reaction schematics illustrated in FIGS. 14 and 15 there is less nanoflower DNA left in the wells of TelN treated concatameric DNA than with VP58.5 treated material. This is because TelN converts both double stranded and singled stranded (nanoflower) DNA into desired closed linear DNA product. This closed linear DNA product has no stem loop or VP58.5 recognition sequences, because the action of the TelN removes these entities as it cleaves the "internal" protelomerase target sites, marked as "B" on the figures, or "3" and "4". This result is also reflected in lane BX compared to lane AX following exonuclease treatment.

The invention claimed is:

1. A cell-free method of producing closed linear deoxyribonucleic acid (DNA) molecules, the method comprising:

(a) contacting a DNA template comprising a linear, double stranded DNA molecule covalently closed at each of its ends by a portion of a protelomerase recognition sequence and comprising at least one stem loop motif with a strand-displacing polymerase under conditions promoting amplification of said DNA template in the presence of at least one primer which is capable of hybridizing specifically to a primer binding site within said stem loop motif; and (b) producing the closed linear DNA molecules by contacting DNA produced in step (a) with at least one protelomerase under conditions promoting production of the closed linear DNA molecules;

wherein a sequence of the stem loop motif comprises a central section and two flanking sequences, and wherein the central section comprises the primer binding site, wherein the sequence of the stem loop motif is capable of forming a stem loop secondary structure under conditions promoting formation of a secondary structure, wherein the central section of the sequence of the stem loop motif is a single stranded DNA region in the stem loop secondary structure, and wherein the sequence of the stem loop motif is different from the portion of the protelomerase recognition sequence of the DNA template, and the stem loop motif and the portion of the protelomerase recognition sequence are located in different parts of the DNA template.

2. The method of claim 1, wherein the sequence of the stem loop motif is adjacent or near to the portion of the protelomerase recognition sequence covalently closed at one of ends of the linear, double stranded DNA molecule.

3. The method of claim 1, wherein the sequence of the stem loop motif includes self-complementary sequences within the two flanking sequences which allow the formation of the stem loop secondary structure.

4. The method of claim 1, wherein, the sequences within the two flanking sequences are being complementary to a bridging oligonucleotide.

5. The method of claim 1, wherein each of the ends of the DNA template comprises the portion of protelomerase recognition sequence and the portion of protelomerase recognition sequence on each of the ends of the DNA template has a different sequence.

6. The method of claim 1, wherein the DNA template comprises one or more additional protelomerase recognition sequences.

7. The method of claim 6, wherein the one or more additional protelomerase recognition sequences comprises two additional protelomerase recognition sequences.

8. The method of claim 7, wherein each of the two additional protelomerase recognition sequences is separated from one of the ends of the linear, double stranded DNA molecule by the at least one stem loop motif.

* * * * *

SEQUENCE LISTING

```
Sequence total quantity: 37
SEQ ID NO: 1              moltype = DNA  length = 1563
FEATURE                   Location/Qualifiers
source                    1..1563
                          mol_type = unassigned DNA
                          note = Source Organism: Halomonas aquamarina phage phiHAP-1
                          organism = unidentified
misc_feature              1..1563
                          note = Protelomerase
SEQUENCE: 1
atgagcggtg agtcacgtag aaaggtcgat ttagcggaat tgatagagtg gttgctcagc  60
gagatcaaag agatcgacgc cgatgatgag atgccacgta aagagaaaac caagcgcatg  120
gcgcggctgg cacgtagctt caaaacgcgc ctgcatgatg acaagcgccg caaggattct  180
gagcggatcg cggtcacgac ctttcgccgc tacatgacag aagcgcgcaa ggcggtgact  240
gcgcagaact ggcgccatca cagcttcgac cagcagatcg agcggctggc cagccgctac  300
ccggcttatg ccagcaagct ggaagcgctc ggcaagctga ccgatatcag cgccattcgt  360
atggcccacc gcgagctgct cgaccagatc cgcaacgatg acgacgctta tgaggacatc  420
cgggcgatga agctggacca tgaaatcatg cgccacctga cgttgagctc tgcacagaaa  480
agcacgctgg ctgaagaggc cagcgagacg ctggaagagc gcgcggtgaa cacggtcgag  540
atcaactacc actggttgat ggagacggtt tacgagctgc tgagtaaccg ggagagaatg  600
gtcgatgggg agtatcgcgg ctttttcagt tacctagcgc ttgggctggc gctggccacc  660
gggcgtcgct cgatcgaggt gctgaagacc ggacggatca cgaaggtggg cgagtatgag  720
ctggagttca gcggccaggc gaaaaagcgc ggcggcgtcg actatagcga ggcttaccac  780
atttataccc tggtgaaagc tgacctggtg atcgaagcgt gggatgagct tcgctcgctg  840
ccggaagctg ctgagctgca gggcatggac aacagcgatg tgaaccgccg cacggcgaag  900
acgctcaaca cgctcactaa gcggatcttt aacaacgatg agcgcgtttt caaggacagc  960
cgggcgatct gggcgcggct ggtgtttgag ctgcacttct cgcgcgacaa gcgctggaag  1020
aaagtcaccg aggacgtgtt ctggcgtgag atgctggggc atgaggacat ggatacacag  1080
cgcagctacc gcgcctttaa aatcgactac gacgagccgg atcaagccga ccaggaagat  1140
tacgaacacg ctagccgcct cgccgcgctg caggcgctgg acggccatga gcagcttgag  1200
agcagcgacg cccaggcgcg tgtgcatgcc tgggtgaaag cgcagatcga gcaggagcct  1260
gacgcgaaaa ttacgcagtc tctgatcagc cgggagctgg gcgtttatcg ccctgccata  1320
aaagcgtacc tggagctggc gcgagaggcg ctcgacgcgc cgaacgtcga tctggacaag  1380
gtcgcggcgg cagtgccgaa ggaagtagcc gaggcgaagc cccggctgaa cgcccaccca  1440
caaggggatg gcaggtgggt cggggtggct tcaatcaacg gggtggaagt tgcacgggtg  1500
ggcaaccagg caggccggat cgaagcgatg aaagcggcct ataaagcggc gggtgggcgc  1560
tga                                                                1563

SEQ ID NO: 2              moltype = AA  length = 520
FEATURE                   Location/Qualifiers
REGION                    1..520
                          note = MISC_FEATURE - Protelomerase
source                    1..520
                          mol_type = protein
                          note = source organism: Halomonas aquamarina phage phiHAP-1
                          organism = unidentified
SEQUENCE: 2
MSGESRRKVD LAELIEWLLS EIKEIDADDE MPRKEKTKRM ARLARSFKTR LHDDKRRKDS  60
ERIAVTTFRR YMTEARKAVT AQNWRHHSFD QQIERLASRY PAYASKLEAL GKLTDISAIR  120
MAHRELLDQI RNDDDAYEDI RAMKLDHEIM RHLTLSSAQK STLAEEASET LEERAVNTVE  180
INYHWLMETV YELLSNRERM VDGEYRGFFS YLALGLALAT GRRSIEVLKT GRITKVGEYE  240
LEFSGQAKKR GGVDYSEAYH IYTLVKADLV IEAWDELRSL PEAAELQGMD NSDVNRRTAK  300
TLNTLTKRIF NNDERVFKDS RAIWARLVFE LHFSRDKRWK KVTEDVFWRE MLGHEDMDTQ  360
RSYRAFKIDY DEPDQADQED YEHASRLAAL QALDGHEQLE SSDAQARVHA WVKAQIEQEP  420
DAKITQSLIS RELGVYRPAI KAYLELAREA LDAPNVDLDK VAAAVPKEVA EAKPRLNAHP  480
QGDGRWVGVA SINGVEVARV GNQAGRIEAM KAAYKAAGGR                      520

SEQ ID NO: 3              moltype = DNA  length = 1854
FEATURE                   Location/Qualifiers
misc_feature              1..1854
```

```
                        note = Protelomerase
source                  1..1854
                        mol_type = unassigned DNA
                        note = source organism: Yersinia enterolytica phage PY54
                        organism = unidentified
SEQUENCE: 3
atgaaaatcc atttcgcgga tttagttagt ggtttagtta aagagatcga tgaaatagaa  60
aaatcagacc gggcgcaggg tgacaaaact cggcgttatc agggcgcggc cagaaagttc  120
aaaaatgccg tgtttatgga taaacggaaa tatcgcggta acggtatgaa gaatagaata  180
tcgttaacaa catttaataa atatttaagt cgagcacgtt ctcggtttga agaaaggctt  240
caccatagtt ttcctcaatc tatagcaact atctcaaata aatatcctgc attcagcgaa  300
ataataaaag atctggataa tagacccgct catgaagtta gaataaaact taaagaatta  360
ataactcatc ttgaatccgg tgttaattta ttagaaaaaa taggtagctt agggaaaata  420
aaaccatcta cagctaaaaa aatagttagc ttaaaaaaaa tgtacccatc atgggctaat  480
gatctagata ctttaattag tactgaagat gctacagaat tacaacaaaa gttagagcaa  540
gggaccgacc tacttaacgc attacattct ctaaaagtaa accatgaagt tatgtatgca  600
ttaacgatgc agccttctga cagagctgca ttaaaagcta ggcatgacgc tgcccttcac  660
tttaaaaagc gtaacatcgt acctatcgat tatcccggct atatgcaacg aatgacggac  720
atactacatc ttccagatat agcttttgaa gattcgatgg catcacttgc ccctttagca  780
tttgctctag cagctgctag cggtcgcaga caaattgaaa tactaattac tggtgagttt  840
gacgccaaaa ataaaagcat cattaaattt tctggacaag caaaaaaaag aatggccgtt  900
tcaggtggac attatgaaat atacagtcta attgactcag agctattcat tcaacggtta  960
gagtttttac gttctcatag ctcaatactt cgattacaaa atttggaaat agcacatgat  1020
gaacatcgta ctgaactatc tgttattaac ggttttgtag ccaaaccttt aaatgatgca  1080
gcaaaacagt tctttgtcga tgacagaaga gtatttaaag atacccgtgc aatttacgct  1140
cgcatagcat atgaaaaatg gtttagaaca gatcctcgct gggcgaagtg cgacgaagat  1200
gttttcttct ctgaattatt aggccatgac gacccagata ctcagctggc atataaacaa  1260
ttcaagctgg taaatttcaa tccaaaatgg acacctaata tatcagatga aaaccctcgg  1320
ttagctgcac ttcaagagct tgacaatgat atgcccggcc tagcacgtgg cgatgcggca  1380
gttcgcatac atgagtgggt taaagagcaa ctggcgcaga accctgcggc aaaaataact  1440
gcataccaaa tcaagaaaaa tttaaattgt cgaaatgact tggccagccg atacatggca  1500
tggtgtgctg acgcgctagg ggttgttatt ggtgatgatg gacaggcaag gccagaagaa  1560
ctcccaccat cgctcgtgct tgatattaac gctgatgaca ctgacgctga agaagatgaa  1620
atagaggaag actttactga tgaggaaata gacgacaccg aattcgacgt atcagataac  1680
gccagtgatg aagataagcc cgaagataaa cctcgctttg cagcaccaat tcgtagaagt  1740
gaggactctt ggctgattaa atttgaattt gctggcaagc aatatagctg ggagggtaat  1800
gccgaaagtg ttatcgatgc gatgaaacaa gcatggactg aaaatatgga gtaa        1854

SEQ ID NO: 4            moltype = AA  length = 617
FEATURE                 Location/Qualifiers
REGION                  1..617
                        note = MISC_FEATURE - Protelomerase
source                  1..617
                        mol_type = protein
                        note = source organism: Yersinia enterolytica phage PY54
                        organism = unidentified
SEQUENCE: 4
MKIHFRDLVS GLVKEIDEIE KSDRAQGDKT RRYQGAARKF KNAVFMDKRK YRGNGMKNRI  60
SLTTFNKYLS RARSRFEERL HHSFPQSIAT ISNKYPAFSE IIKDLDNRPA HEVRIKLKEL  120
ITHLESGVNL LEKIGSLGKI KPSTAKKIVS LKKMYPSWAN DLDTLISTED ATELQQKLEQ  180
GTDLLNALHS LKVNHEVMYA LTMQPSDRAA LKARHDAALH FKKRNIVPID YPGYMQRMTD  240
ILHLPDIAFE DSMASLAPLA FALAAASGRR QIEILITGEF DAKNKSIIKF SGQAKKRMAV  300
SGGHYEIYSL IDSELFIQRL EFLRSHSSIL RLQNLEIAHD EHRTELSVIN GFVAKPLNDA  360
AKQFFVDDRR VFKDTRAIYA RIAYEKWFRT DPRWAKCDED VFFSELLGHD DPDTQLAYKQ  420
FKLVNFNPKW TPNISDENPR LAALQELDND MPGLARGDAA VRIHEWVKEQ LAQNPAAKIT  480
AYQIKKNLNC RNDLASRYMA WCADALGVVI GDDGQARPEE LPPSLVLDIN ADDTDAEEDE  540
IEEDFTDEEI DDTEFDVSDN ASDEDKPEDK PRFAAPIRRS EDSWLIKFEF AGKQYSWEGN  600
AESVIDAMKQ AWTENME                                                617

SEQ ID NO: 5            moltype = DNA  length = 1923
FEATURE                 Location/Qualifiers
misc_feature            1..1923
                        note = Protelomerase
source                  1..1923
                        mol_type = unassigned DNA
                        note = source organism: Klebsiella phage phiKO2
                        organism = unidentified
SEQUENCE: 5
atgcgtaagg tgaaaattgg tgagctaatc aattcgcttg tgagcgaggt cgaggcaatc  60
gatgcctctg atcgtccgca aggcgataaa acgaagaaaa ttaaagccgc agcattaaaa  120
tataagaatg cattatttaa tgacaaaaga aagtttcgcg gtaaaggttt agaaaaaaga  180
atttctgcca acacgttcaa ctcgtatatg agtcgggcaa ggaaaagatt tgatgataga  240
ttgcatcata actttgaaaa gaatgtaatt aaactatcag aaaaatatcc tttatatagt  300
gaagaattat cttcgtggct ttctatgcct gcggcatcaa ttagacagca tatgtcaaga  360
ttgcaagcca agctaaaaga gataatgcca ttggcagaag acttatccaa tataaagatt  420
ggtacaaaaa atagcgaagc aaaaataaat aaactcgcta ataaatatcc tgaatggcaa  480
ttcgctatta gtgatttaaa tagcgaagat tggaaggata aaagagatta tctttataaa  540
ctattccaac aaggttcttc gctcctggaa gacttgaata acctgaaagt aaaccatgag  600
gttctctatc atctgcagct tagttctgcc gagcgaacct ctatccagca gcgctgggcc  660
```

```
aacgtcctca gcgagaaaaa gcgcaacgtt gtcgtgattg actatccgcg ctatatgcag  720
gccatctacg atataatcaa caagcctata gtttcgttcg atttgactac tcgtcgtggt  780
atggccccgc tggcgttcgc ccttgccgcg ctatctggtc gccgaatgat tgaaatcatg  840
ctccagggtg aattttccgt cgcaggtaaa tatacagtaa cattcctggg gcaagctaaa  900
aaacgctcgg aagataaagg tatatcaagg aaaatatata ccttatgcga cgctacttta  960
tttgttagtt tggtaaatga acttcgctca tgccccgctg ctgcggattt tgatgaagta  1020
ataaaaggat atggcgaaaa tgacactcgc tcagaaaatg ggcgtattaa tgcaattctc  1080
gctacagctt ttaatccgtg ggtaaaaact ttcttaggcg atgaccgccg cgtttataaa  1140
gatagccgcg ctatttacgc ccgtattgcc tatgaaatgt tcttccgcgt tgaccctcgg  1200
tggaagaatg ttgatgagga tgtattcttc atggagattc tcggccatga cgatgaaaac  1260
acccaactgc actataagca gtttaaattg gctaacttct ccagaacatg gcgaccaaat  1320
gtcggcgagg agaatgcccg cctagcggcg ctgcaaaagc tggatagcat gatgccagat  1380
tttgccaggg gcgacgccgg ggttcgtatt catgagaccg tgaagcagct ggtggagcag  1440
gacccatcga taaaaatcac aaacagcacc ctgcgaccgt ttaacttcag taccaggctg  1500
attcctcgct acctggagtt tgccgccgat gcattgggcc agttcgtcgg tgaaaatggg  1560
caatggcaac tgaaggatga ggcgcctgca atagtcctgc ctgatgagga aattcttgag  1620
cctatggacg acgtcgatct cgatgacgaa aaccatgatg atgaaacgct ggatgacgat  1680
gagatcgaag tggacgaaag cgaaggagag gaactggagg aagcgggcga cgctgaagag  1740
gccgaggtgg ctgaacagga agagaagcac cctggcaagc caaactttaa agcgccgagg  1800
gataatggcg atggtaccta catggtggaa tttgaattcg gtggccgtca ttacgcctgg  1860
tccggtgccg ccggtaatcg ggtagaggca atgcaatctg cctggagtgc ctacttcaag  1920
tga                                                                1923
```

```
SEQ ID NO: 6          moltype = AA  length = 640
FEATURE               Location/Qualifiers
REGION                1..640
                      note = MISC_FEATURE - Protelomerase
source                1..640
                      mol_type = protein
                      note = source organism: Klebsiella phage phiKO2
                      organism = unidentified
SEQUENCE: 6
MRKVKIGELI NSLVSEVEAI DASDRPQGDK TKKIKAAALK YKNALFNDKR KFRGKGLEKR  60
ISANTFNSYM SRARKRFDDR LHHNFEKNVI KLSEKYPLYS EELSSWLSMP AASIRQHMSR  120
LQAKLKEIMP LAEDLSNIKI GTKNSEAKIN KLANKYPEWQ FAISDLNSED WKDKRDYLYK  180
LFQQGSSLLE DLNNLKVNHE VLYHLQLSSA ERTSIQQRWA NVLSEKKRNV VVIDYPRYMQ  240
AIYDIINKPI VSFDLTTRRG MAPLAFALAA LSGRRMIEIM LQGEFSVAGK YTVTFLGQAK  300
KRSEDKGISR KIYTLCDATL FVSLVNELRS CPAAADFDEV IKGYGENDTR SENGRINAIL  360
ATAFNPWVKT FLGDDRRVYK DSRAIYARIA YEMFFRVDPR WKNVDEDVFF MEILGHDDEN  420
TQLHYKQFKL ANFSRTWRPN VGEENARLAA LQKLDSMMPD FARGDAGVRI HETVKQLVEQ  480
DPSIKITNST LRPFNFSTRL IPRYLEFAAD ALGQFVGENG QWQLKDEAPA IVLPDEEILE  540
PMDDVDLDDE NHDDETLDDD EIEVDESEGE ELEEAGDAEE AEVAEQEEKH PGKPNFKAPR  600
DNGDGTYMVE FEFGGRHYAW SGAAGNRVEA MQSAWSAYFK                         640
```

```
SEQ ID NO: 7          moltype = DNA  length = 1617
FEATURE               Location/Qualifiers
misc_feature          1..1617
                      note = Protelomerase
source                1..1617
                      mol_type = unassigned DNA
                      note = source organsim: Vibrio sp. phage VP882
                      organism = unidentified
SEQUENCE: 7
atgagcggcg aaagtagaca aaaggtaaac ctcgaggagt taataaatga gctcgtcgag  60
gaggtgaaaa ccatcgatga caatgaggcg attactcggt ctgaaaaaac caagttgatc  120
accagggcgg cgactaaatt caagaccaag ctgcacgacg ataagcgccg gaaggatgcg  180
accagaatcg ctctgagcac ctatcgtaag tacatgacaa tggccagggc agcagttact  240
gagcagaact ggaaacacca cagtctcgag cagcagatag agcggctggc caaaaagcac  300
ccgcaatacg ctgagcagct ggtggccatc ggggccatgg ataacatcac cgagttgcgc  360
ctggcgcatc gcgacctcct gaagagcatc aaggacaacg atgaagcctt cgaggatatc  420
cgcagcatga agttagacca cgaggtaatg cgccatctga cgctacccag tgcgcaaaag  480
gcgagactgg cagaggaagc cgccgaggcg ttgaccgaga agaaaaccgc cacggtcgac  540
atcaactatc acgagctgat ggccggcgtg gtggagctgt tgaccaagaa gaccaagacg  600
gtcggcagcg acagcaccta cagcttcagc cggctggcgc ttggtattgg cctggctacc  660
ggtcgtcgtt ctatcgagat actgaagcag ggcgagttca aaaaggtgga tgagcagcgg  720
ctcgagttct ctggccaagc gaaaaagcgc ggcggtgccg actattcaga gacctatacc  780
atttacaccc tggtcgactc cgacctggta ctgatggcgc tgaagaacct gcgagagttg  840
ccagaagttc gcgcactgga tgagtacgac caactgggcg agattaagcg gaacgacgcc  900
atcaataaac gctgtgcaaa aacgctcaac caaaccgcca agcagttctt tggcagcgac  960
gagcgcgtgt tcaaagatag tcgtgccatc tgggcgcgtc tggcttatga gttgtttttt  1020
caacgtgatc cgcgctggaa aaagaaagac gaggacgttt tctggcagga gatgctgggc  1080
cacgaggaca tcgagactca gaaagcctat aagcaattca aggtcgacta cagcgaacct  1140
gagcagccgg tgcacaagcc tggcaaattt aagagcagag ctgaagccct cgcggcgctc  1200
gactcaaatg aggacattac cacccgctca tccatggcca agatccacga ctgggtgaaa  1260
gagcgtattg cggaagaccc cgaggcgaac atcacacagt cactcatcac ccgggaactg  1320
ggctcaggcc gtaaggtgat caaggactac ctcgacctgg ctgacgatgc ccttgctgtg  1380
gtgaatactc ctgtcgatga cgcagtcgtc gaggttccag ctgatgtgcc ggcagcagaa  1440
aaacagccga agaaagcgca gaagcccaga ctcgtggctc accaggttga tgatgagcac  1500
tgggaagcct gggcgctggt ggaaggcgag gaggtggcca gggtgaaaat caagggcacc  1560
```

```
cgcgttgagg caatgacagc cgcatgggag gccagccaaa aggcactcga tgactaa     1617

SEQ ID NO: 8           moltype = AA  length = 538
FEATURE                Location/Qualifiers
REGION                 1..538
                       note = MISC_FEATURE - Protelomerase
source                 1..538
                       mol_type = protein
                       note = source organism: Vibrio sp. phage VP882
                       organism = unidentified
SEQUENCE: 8
MSGESRQKVN LEELINELVE EVKTIDDNEA ITRSEKTKLI TRAATKFKTK LHDDKRRKDA  60
TRIALSTYRK YMTMARAAVT EQNWKHHSLE QQIERLAKKH PQYAEQLVAI GAMDNITELR  120
LAHRDLLKSI KDNDEAFEDI RSMKLDHEVM RHLTLPSAQK ARLAEEAAEA LTEKKTATVD  180
INYHELMAGV VELLTKKTKT VGSDSTYSFS RLALGIGLAT GRRSIEILKQ GEFKKVDEQR  240
LEFSGQAKKR GGADYSETYT IYTLVDSDLV LMALKNLREL PEVRALDEYD QLGEIKRNDA  300
INKRCAKTLN QTAKQFFGSD ERVFKDSRAI WARLAYELFF QRDPRWKKKD EDVFWQEMLG  360
HEDIETQKAY KQFKVDYSEP EQPVHKPGKF KSRAEALAAL DSNEDITTRS SMAKIHDWVK  420
ERIAEDPEAN ITQSLITREL GSGRKVIKDY LDLADDALAV VNTPVDDAVV EVPADVPAAE  480
KQPKKAQKPR LVAHQVDDEH WEAWALVEGE EVARVKIKGT RVEAMTAAWE ASQKALDD    538

SEQ ID NO: 9           moltype = DNA  length = 4055
FEATURE                Location/Qualifiers
misc_feature           1..4055
                       note = Protelomerase TelN
source                 1..4055
                       mol_type = other DNA
                       note = source organism: Escherichia coli bacteriophage N15
                       organism = unidentified
SEQUENCE: 9
catatgcact atatcatatc tcaattacgg aacatatcag cacacaattg cccattatac  60
gcgcgtataa tggactattg tgtgctgata aggagaacat aagcgcagaa caatatgtat  120
ctattccggt gttgtgttcc tttgttattc tgctattatg ttctcttata gtgtgacgaa  180
agcagcataa ttaatcgtca cttgttcttt gattgtgtta cgatatccag agacttagaa  240
acgggggaac cgggatgagc aaggtaaaaa tcggtgagtt gatcaacacg cttgtgaatg  300
aggtagaggc aattgatgcc tcagaccgcc cacaaggcga caaaacgaag agaattaaag  360
ccgcagccgc acggtataag aacgcgttat ttaatgataa aagaaagttc cgtgggaaag  420
gattgcagaa aagaataacc gcgaatactt ttaacgccta tatgagcagg gcaagaaagc  480
ggtttgatga taaattacat catagctttg ataaaaatat taataaatta tcggaaaagt  540
atcctcttta cagcgaagaa ttatcttcat ggctttctat gcctacggct aatattcgcc  600
agcacatgtc atcgttacaa tctaaattga aagaaataat gccgcttgcc gaagagttat  660
caaatgtaag aataggctct aaaggcagtg atgcaaaaat agcaagacta ataaaaaaat  720
atccagattg gagttttgct cttagtgatt taaacagtga tgattggaag gagcgccgtg  780
actatcttta taagttattc caacaaggct ctgcgttgtt agaagaacta caccagctca  840
aggtcaacca tgaggttctg taccatctgc agctaagccc tgcggagcgt acatctatac  900
agcaacgatg ggccgatgtt ctgcgcgaga agaagcgtaa tgttgtggtt attgactacc  960
caacatacat gcagtctatc tatgatattt tgaataatcc tgcgacttta tttagtttaa  1020
acactcgttc tggaatggca cctttggcct ttgctctggc tgcggtatca gggcgaagaa  1080
tgattgagat aatgtttcag ggtgaatttg ccgtttcagg aaagtatacg gttaatttct  1140
cagggcaagc taaaaaacgc tctgaagata aaagcgtaac cagaacgatt tatactttat  1200
gcgaagcaaa attattcgtt gaattattaa cagaattgcg ttcttgctct gctgcatctg  1260
atttcgatga ggttgttaaa ggatatggaa aggatgatac aaggtctgag aacggcagga  1320
taaatgctat tttagcaaaa gcatttaacc cttgggttaa atcatttttc ggcgatgacc  1380
gtcgtgttta taaagatagc cgcgctattt acgctcgcat cgcttatgag atgttcttcc  1440
gcgtcgatcc acggtggaaa aacgtcgacg aggatgtgtt cttcatggag attctcggac  1500
acgacgatga gaacacccag ctgcactata agcagttcaa gctggccaac ttctccagaa  1560
cctggcgacc tgaagttggg gatgaaaaca ccaggctggt ggctctgcag aaactggacg  1620
atgaaatgcc aggctttgcc agaggtgacg ctggcgtccg tctccatgaa accgttaagc  1680
agctggtgga gcaggaccca tcagcaaaaa taaccaacag cactctccgg gcctttaaat  1740
ttagcccgac gatgattagc cggtacctgg agtttgccgc tgatgcattg gggcagttcg  1800
ttggcgagaa cgggcagtgg cagctgaaga tagagacacc tgcaatcgtc ctgcctgatg  1860
aagaatccgt tgagaccatc gacgaaccgg atgatgagtc ccaagacgac gagctggatg  1920
aagatgaaat tgagctcgac gagggtggcg gcgatgaacc aaccgaagag gaagggccag  1980
aagaacatca gccaactgct ctaaaacccg tcttcaagcc tgcaaaaaat aacggggacg  2040
gaacgtacaa gatagagttt gaatacgatg gaaagcatta tgcctggtcc ggccccgccg  2100
atagccctat ggccgcaatg cgatccgcat gggaaacgta ctacagctaa aagaaaagcc  2160
accggtgtta atcggtggct tttttattga ggcctgtccc tacccatccc ctgcaaggga  2220
cggaaggatt aggcggaaac tgcagctgca actacggaca tcgccgtccc gactgcaggg  2280
acttccccgc gtaaagcggg gcttaaattc gggctggcca accctatttt tctgcaatcg  2340
ctggcgatgt tagtttcgtg gatagcgttt ccagcttttc aatggccagc tcaaaatgtg  2400
ctggcagcac cttctccagt tccgtatcaa tatcggtgat cggcagctct ccacaagaca  2460
tactccggcg accgccacga actacatcgc gcagcagctc ccgttcgtag acacgcatgt  2520
tgcccagagc cgtttctgca gccgttaata tccggcgcac gtcggcgatg attgccggga  2580
gatcatccac ggttattggg ttcggtgatg ggttcctgca ggcgcggcgg agagccatcc  2640
agacgccgct aacccatgcg ttacggtact gaaaactttg tgctatgtcg tttatcaggc  2700
ccgaagttct tctttctgcc gccagtccag tggttcaccg gcgttcttag gctcaggctc  2760
gacaaaagca tactcgccgt tttttccggat agctggcaga acctcgttcg tcacccactt  2820
gcggaaccgc caggctgtcg tcccctgttt caccgcgtcg cggcagcgga ggattatggt  2880
gtagagacca gattccgata ccacatttac ttccctggcc atccgatcaa gtttttgtgc  2940
```

```
ctcggttaaa ccgagggtca atttttcatc atgatccagc ttacgcaatg catcagaagg  3000
gttggctata ttcaatgcag cacagatatc cagcgccaca aaccacgggt caccaccgac  3060
aagaaccacc cgtatagggt ggctttcctg aaatgaaaag acggagagag ccttcattgc  3120
gcctccccgg atttcagctg ctcagaaagg gacagggagc agccgcgagc ttcctgcgtg  3180
agttcgcgcg cgacctgcag aagttccgca gcttcctgca aatacagcgt ggcctcataa  3240
ctggagatag tgcggtgagc agagcccaca agcgcttcaa cctgcagcag gcgttcctca  3300
atcgtctcca gcaggccctg ggcgtttaac tgaatctggt tcatgcgatc acctcgctga  3360
ccgggatacg ggctgacaga acgaggacaa aacggctggc gaactggcga cgagcttctc  3420
gctcggatga tgcaatggtg gaaaggcggt ggatatggga ttttttgtcc gtgcggacga  3480
cagctgcaaa tttgaatttg aacatggtat gcattcctat cttgtatagg gtgctaccac  3540
cagagttgag aatctctata ggggtggtag cccagacagg gttctcaaca ccggtacaag  3600
aagaaaccgg cccaaccgaa gttggcccca tctgagccac cataattcag gtatgcgcag  3660
atttaacaca caaaaaaaca cgctggcgcg tgttgtgcgc ttcttgtcat tcggggttga  3720
gaggcccggc tgcagatttt gctgcagcgg ggtaactcta ccgccaaagc agaacgcacg  3780
tcaataattt aggtggatat ttaccccgt gaccagtcac gtgcacaggt gtttttatag  3840
tttgctttac tgactgatca gaacctgatc agttattgga gtccggtaat cttattgatg  3900
accgcagcca ccttagatgt tgtctcaaac cccatacggc cacgaatgag ccactggaac  3960
ggaatagtca gcaggtacag cggaacgaac cacaaacggt tcagacgctg ccagaacgtc  4020
gcatcacgac gttccatcca ttcggtattg tcgac                            4055
```

```
SEQ ID NO: 10          moltype = AA  length = 631
FEATURE                Location/Qualifiers
REGION                 1..631
                       note = misc_feature - Protelomerase sequence Tel N
source                 1..631
                       mol_type = protein
                       note = source organism: Escherichia coli bacteriophage N15
                       organism = unidentified
SEQUENCE: 10
MSKVKIGELI NTLVNEVEAI DASDRPQGDK TKRIKAAAAR YKNALFNDKR KFRGKGLQKR  60
ITANTFNAYM SRARKRFDDK LHHSFDKNIN KLSEKYPLYS EELSSWLSMP TANIRQHMSS  120
LQSKLKEIMP LAEELSNVRI GSKGSDAKIA RLIKKYPDWS FALSDLNSDD WKERRDYLYK  180
LFQQGSALLE ELHQLKVNHE VLYHLQLSPA ERTSIQQRWA DVLREKKRNV VVIDYPTYMQ  240
SIYDILNNPA TLFSLNTRSG MAPLAFALAA VSGRRMIEIM FQGEFAVSGK YTVNFSGQAK  300
KRSEDKSVTR TIYTLCEAKL FVELLTELRS CSAASDFDEV VKGYGKDDTR SENGRINAIL  360
AKAFNPWVKS FFGDDRRVYK DSRAIYARIA YEMFFRVDPR WKNVDEDVFF MEILGHDDEN  420
TQLHYKQFKL ANFSRTWRPE VGDENTRLVA LQKLDDEMPG FARGDAGVRL HETVKQLVEQ  480
DPSAKITNST LRAFKFSPTM ISRYLEFAAD ALGQFVGENG QWQLKIETPA IVLPDEESVE  540
TIDEPDDESQ DDELDEDEIE LDEGGGDEPT EEEGPEEHQP TALKPVFKPA KNNGDGTYKI  600
EFEYDGKHYA WSGPADSPMA AMRSAWETYY S                                631
```

```
SEQ ID NO: 11          moltype = DNA  length = 1329
FEATURE                Location/Qualifiers
misc_feature           1..1329
                       note = Protelomerase TelA
source                 1..1329
                       mol_type = unassigned DNA
                       note = source organism: Agrobacterium tumefaciens strain C58
                       organism = unidentified
SEQUENCE: 11
atgctcgccg caaaacgaaa aacaaaaaca ccggtcctcg tggaacgcat cgatcaattc  60
gtcggccaga tcaaagaggc gatgaaaagc gacgacgctt cgcgaaacag gaaaatccgc  120
gatctgtggg atgccgaggt ccgctatcat ttcgataatg gccgcacgga aaagacgctc  180
gaactttaca tcatgaaata tcgcaatgcg ctgaaggccg aattcggccc gaagagcacc  240
ccgctagcca tctgcaacat gaagaagctg cgcgagcgcc tgaacaccta tattgcccgg  300
ggcgattatc ccaagacagg cgtggcgacg tcgattgtcg aaaaaatcga gcgggcggag  360
ttcaacaccg ccggccgcaa acccacggtt ctccttcgca tagccgattt cattgccgcg  420
atgaacggca tggacgcgaa gcaggacatg caggctctgt gggacgcaga aatcgccatc  480
atgaacggcc gcgcccagac gacgatcatt tcctacatca ccaaatatcg caacgccatc  540
cgggaagcct tcggtgacga ccatccgatg ctgaagatcg ccaccggcga tgccgcgatg  600
tatgacgagg cccgccgggt gaagatggag aagatcgcca acaagcatgg cgcgctcatc  660
acattcgaga actaccggca ggttctgaaa atctgcgagg attgtctcaa gtccagcgat  720
cccctgatga tcggcatcgg cctcatcggc atgacgggac gccgacccta tgaagtcttc  780
acccaggcgg aattttcacc tgcaccctat ggcaagggag tttccaaatg gagcatcctg  840
ttcaacggtc aggccaagac gaaacagggc gagggcacga aattcgggat tacctatgaa  900
attcctgtcc tgacgcgctc cgaaaccgtg ctggctgcct ataagcgcct gcgcgaaagc  960
ggacagggaa aattatggca tggcatgtcg atcgacgatt tttcctcgga aacccgcctg  1020
ctgctgcgcg acacggtttt taacctgttc gaggatgtct ggccaaagga agagcttccc  1080
aagccctatg gcctcagaca cctctatgcc gaagtggcct atcacaattt cgcgccaccc  1140
catgtcacca agaacagcta tttcgccgcc attcttggcc acaacaataa cgacctcgaa  1200
acgtcgctgt cctatatgac ctatacgctg ccggaagacc gcgacaatgc gctggcgcgc  1260
ctgaagcgga ccaatgagcg gacattgcag caaatggcga cgatcgcgcc cgtgtcccgc  1320
aagggatga                                                         1329
```

```
SEQ ID NO: 12          moltype = AA  length = 442
FEATURE                Location/Qualifiers
REGION                 1..442
                       note = MISC_FEATURE - Protelomerase TelA
source                 1..442
```

```
                        mol_type = protein
                        note = source organism: Agrobacterium tumefaciens strain C58
                        organism = unidentified
SEQUENCE: 12
MLAAKRKTKT PVLVERIDQF VGQIKEAMKS DDASRNRKIR DLWDAEVRYH FDNGRTEKTL  60
ELYIMKYRNA LKAEFGPKST PLAICNMKKL RERLNTYIAR GDYPKTGVAT SIVEKIERAE  120
FNTAGRKPTV LLRIADFIAA MNGMDAKQDM QALWDAEIAI MNGRAQTTII SYITKYRNAI  180
REAFGDDHPM LKIATGDAAM YDEARRVKME KIANKHGALI TFENYRQVLK ICEDCLKSSD  240
PLMIGIGLIG MTGRRPYEVF TQAEFSPAPY GKGVSKWSIL FNGQAKTKQG EGTKFGITYE  300
IPVLTRSETV LAAYKRLRES GQGKLWHGMS IDDFSSETRL LLRDTVFNLF EDVWPKEELP  360
KPYGLRHLYA EVAYHNFAPP HVTKNSYFAA ILGHNNNDLE TSLSYMTYTL PEDRDNALAR  420
LKRTNERTLQ QMATIAPVSR KG                                          442

SEQ ID NO: 13           moltype = DNA  length = 1668
FEATURE                 Location/Qualifiers
misc_feature            1..1668
                        note = Protelomerase
source                  1..1668
                        mol_type = unassigned DNA
                        note = source organism: Vibrio parahaemolyticus phage
                         Vp58.5 Gp40
                        organism = unidentified
SEQUENCE: 13
atgaaactaa ctgacggaat ggaccgcaca aagtacatcg ttaaagcggc caaacatatc  60
caagaagaag gtcaagaaaa gggacctaaa tacatcactg accgctgcgg tcgtgtcgct  120
aaggatgagc acaaacgtct tggctgggtt gtggaccagg tgtcaggtga gctggccagc  180
aatccacaaa tcagccataa ccactatatc aatcttatga ataattaccg tagagccatc  240
aaggccctag ggtataagca tcaccaaata gaaaagacat tagtaacttt tatcaataaa  300
tatcaagaat atagacctga aatagcagag atgctggacc catctttgcc aattgatacc  360
ttgagagaga atgtgatcct tctgaaatca caggccaggt caaaaagtga atttcgtagt  420
gacctgcttg gtcttcgcat tgagtttcac ctctactatc tgtttgaacc aaagggcatt  480
gcaaccgata agcgcaaaga gcaagtaaaa gaagcgttga atgaaaagca tgagaacgtc  540
atcaagataa atggcgatca catcaaggaa ctggccacaa aaattctgtc agaaaaggac  600
ccgtcatata cagaccttgc agttggcctt gctcttgcga ctggccgtcg agctaatgag  660
attatgaaga ctgccagctt taagaaatca ggtgaacggt cgcttatgtt tgagggacag  720
ctaaaaaccc ataaccgata cctgtttgaa gaaattggag catacgagat accttgtatt  780
gttgattcag acttagtaat taaaggattg aaattattaa gaaaaaaaac aggagcggaa  840
atcctggaat atactgatgt cactggacgt acagttaaaa aggctgttgc tgacggcgac  900
actaaggacc tgagacacaa tgatgcagtc aaccttcggt tcactgcatc acttaaccag  960
agagtcaagg ccatactagg ccatggagag tttagtttca ggacctgtcg ggccatctat  1020
gtcgaaatag cattccatga gttcagacat aacggagaat cgaaagcggc cttccgtagc  1080
agagttcttg gccactcagg tggtgataaa tcaacacaga accactatga ggggtttgag  1140
cttgattcca aggtggaaac catcggtgtg gttgatatgg gccaaaacga ggctgacaag  1200
tcatacaaca agcaactgct gaagcacctg gagcaatacg atgcaacaat tgcagcctat  1260
ctgagagcgc ctaactggaa acacattcat gattggctaa aagaccaggt gaaaaacggc  1320
ctgcagcttg accaaataac cacaagctat ctgagaaaaa tgtgcatcat caacaacaaa  1380
agcctcaatg caaacaccat cgccaagtac ctggaaacat tgaacctaga taaggttcca  1440
gcagagcaag aggaaagcca tcaggaagaa ctggagcagg aagaagatca gaaagtgtca  1500
tggccaaaag ctaaagacat taaggtccag tctaaaaaag aaggtgatat gtggcatgtc  1560
tggactgagg ttaacggaat gcggtgggaa aattggtcta aaggtagaaa aacagaagct  1620
gtgaaggcat tgcgacaaca atatgagagg gaatcagcgg aaatgtaa              1668

SEQ ID NO: 14           moltype = AA  length = 555
FEATURE                 Location/Qualifiers
REGION                  1..555
                        note = MISC_FEATURE - Protelomerase
source                  1..555
                        mol_type = protein
                        note = source organism: Vibrio parahaemolyticus phage
                         Vp58.5 Gp40
                        organism = unidentified
SEQUENCE: 14
MKLTDGMDRT KYIVKAAKHI QEEGQEKGPK YITDRCGRVA KDEHKRLGWV VDQVSGELAS  60
NPQISHNHYI NLMNNYRRAI KALGYKHHQI EKTLVTFINK YQEYRPEIAE MLDPSLPIDT  120
LRENVILLKS QARSKSEFRS DLLGLRIEFH LYYLFEPKGI ATDKRKEQVK EALNEKHENV  180
IKINGDHIKE LATKILSEKD PSYTDLAVGL ALATGRRANE IMKTASFKKS GERSLMFEGQ  240
LKTHNRYLFE EIGAYEIPCI VDSDLVIKGL KLLRKKTGAE ILEYTDVTGR TVKKAVADGD  300
TKDLRHNDAV NLRFTASLNQ RVKAILGHGE FSFRTCRAIY VEIAFHEFRH NGESKAAFRS  360
RVLGHSGGDK STQNHYEGFE LDSKVETIGV VDMGQNEADK SYNKQLLKHL EQYDATIAAY  420
LRAPNWKHIH DWLKDQVKNG LQLDQITTSY LRKMCIINNK SLNANTIAKY LETLNLDKVP  480
AEQEESHQEE LEQEEDQKVS WPKAKDIKVQ SKKEGDMWHV WTEVNGMRWE NWSKGRKTEA  540
VKALRQQYER ESAEM                                                  555

SEQ ID NO: 15           moltype = DNA  length = 56
FEATURE                 Location/Qualifiers
misc_feature            1..56
                        note = protelomerase target sequence
source                  1..56
                        mol_type = unassigned DNA
```

```
                          note = source organism: Escherichia coli phage N15
                          organism = unidentified
SEQUENCE: 15
tatcagcaca caattgccca ttatacgcgc gtataatgga ctattgtgtg ctgata      56

SEQ ID NO: 16             moltype = DNA  length = 50
FEATURE                   Location/Qualifiers
misc_feature              1..50
                          note = protelomerase target sequence
source                    1..50
                          mol_type = unassigned DNA
                          note = source organism: Klebsiella phage phiK02
                          organism = unidentified
SEQUENCE: 16
cagcacacaa cagcccatta tacgcgcgta taatgggcta ttatgtgctg            50

SEQ ID NO: 17             moltype = DNA  length = 52
FEATURE                   Location/Qualifiers
misc_feature              1..52
                          note = protelomerase target sequence
source                    1..52
                          mol_type = unassigned DNA
                          note = source organsim: Yersinia enterolytica phage PY54
                          organism = unidentified
SEQUENCE: 17
tagtcaccta tttcagcata ctacgcgcgt agtatgctga aataggttac tg         52

SEQ ID NO: 18             moltype = DNA  length = 90
FEATURE                   Location/Qualifiers
misc_feature              1..90
                          note = protelomerase target sequence
source                    1..90
                          mol_type = unassigned DNA
                          note = source organism: Vibrio sp. phage VP882
                          organism = unidentified
SEQUENCE: 18
gggatcccgt tccatacata catgtatcca tgtggcatac tatacgtata gtatgccgat  60
gttacatatg gtatcattcg ggatcccgtt                                  90

SEQ ID NO: 19             moltype = DNA  length = 38
FEATURE                   Location/Qualifiers
misc_feature              1..38
                          note = protelomerase target sequence
source                    1..38
                          mol_type = unassigned DNA
                          organism = Borrelia burgdorferi
SEQUENCE: 19
tactaaataa atattatata tataattttt tattagta                         38

SEQ ID NO: 20             moltype = DNA  length = 50
FEATURE                   Location/Qualifiers
misc_feature              1..50
                          note = protelomerase target sequence
source                    1..50
                          mol_type = unassigned DNA
                          note = source organism: Agrobacterium tumefaciens strain C58
                          organism = unidentified
SEQUENCE: 20
gcgatcgatc ataataacaa tatcatgata ttgttattgt aatcgatcgc            50

SEQ ID NO: 21             moltype = DNA  length = 56
FEATURE                   Location/Qualifiers
misc_feature              1..56
                          note = protelomerase target sequence
source                    1..56
                          mol_type = unassigned DNA
                          note = source organism: Vibrio parahaemolyticus phage
                           Vp58.5 Gp40
                          organism = unidentified
SEQUENCE: 21
aacctgcaca ggtgtacata tagtctaatt agactatatg tacacctgtg caggtt      56

SEQ ID NO: 22             moltype = DNA  length = 26
FEATURE                   Location/Qualifiers
misc_feature              1..26
                          note = protelomerase target sequence
source                    1..26
                          mol_type = unassigned DNA
                          note = source organism: Agrobacterium tumefaciens strain C58
```

```
                        organism = unidentified
SEQUENCE: 22
aataacaata tcatgatatt gttatt                                    26

SEQ ID NO: 23           moltype = DNA  length = 65
FEATURE                 Location/Qualifiers
misc_feature            1..65
                        note = stem loop motif
source                  1..65
                        mol_type = other DNA
                        organism = synthetic construct
SEQUENCE: 23
gggcggtcgg ctgcgcgcgt gggccaagtc tccctacaag ggcccacgcg cgcagccgac  60
cgccc                                                              65

SEQ ID NO: 24           moltype = DNA  length = 75
FEATURE                 Location/Qualifiers
misc_feature            1..75
                        note = stem loop motif
source                  1..75
                        mol_type = other DNA
                        organism = synthetic construct
SEQUENCE: 24
gggcggtcgg ctgcgcgcgt gggccaaaaa aagtctccct acaagaaaaa ggcccacgcg  60
cgcagccgac cgccc                                                   75

SEQ ID NO: 25           moltype = DNA  length = 75
FEATURE                 Location/Qualifiers
misc_feature            1..75
                        note = stem loop motif
source                  1..75
                        mol_type = other DNA
                        organism = synthetic construct
SEQUENCE: 25
gggcggtcgg ctgcgcgcgt gggccaaaaa aaaaaaagtc tccctacaag ggcccacgcg  60
cgcagccgac cgccc                                                   75

SEQ ID NO: 26           moltype = DNA  length = 75
FEATURE                 Location/Qualifiers
misc_feature            1..75
                        note = stem loop motif
source                  1..75
                        mol_type = other DNA
                        organism = synthetic construct
SEQUENCE: 26
gggcggtcgg ctgcgcgcgt gggccaagtc tccctacaag aaaaaaaaaa ggcccacgcg  60
cgcagccgac cgccc                                                   75

SEQ ID NO: 27           moltype = DNA  length = 45
FEATURE                 Location/Qualifiers
misc_feature            1..45
                        note = stem loop motif
source                  1..45
                        mol_type = other DNA
                        organism = synthetic construct
SEQUENCE: 27
gggcggtcgg gtgcgaagtc tccctacaag cgcacccgac cgccc                  45

SEQ ID NO: 28           moltype = DNA  length = 55
FEATURE                 Location/Qualifiers
misc_feature            1..55
                        note = stem loop motif
source                  1..55
                        mol_type = other DNA
                        organism = synthetic construct
SEQUENCE: 28
gggcggtcgg gtgcgaaaaa aagtctccct acaagaaaaa cgcacccgac cgccc       55

SEQ ID NO: 29           moltype = DNA  length = 55
FEATURE                 Location/Qualifiers
misc_feature            1..55
                        note = stem loop motif
source                  1..55
                        mol_type = other DNA
                        organism = synthetic construct
SEQUENCE: 29
gggcggtcgg gtgcgaaaaa aaaaaaagtc tccctacaag cgcacccgac cgccc       55

SEQ ID NO: 30           moltype = DNA  length = 55
```

-continued

```
FEATURE                 Location/Qualifiers
misc_feature            1..55
                        note = stem loop motif
source                  1..55
                        mol_type = other DNA
                        organism = synthetic construct
SEQUENCE: 30
gggcggtcgg gtgcgaagtc tccctacaag aaaaaaaaaa cgcacccgac cgccc      55

SEQ ID NO: 31           moltype = DNA  length = 41
FEATURE                 Location/Qualifiers
misc_feature            1..41
                        note = stem loop motif figure 10a
source                  1..41
                        mol_type = other DNA
                        organism = synthetic construct
SEQUENCE: 31
aaatataaac ctaaagtctc cctacaagta agtttatatt t                       41

SEQ ID NO: 32           moltype =   length =
SEQUENCE: 32
000

SEQ ID NO: 33           moltype =   length =
SEQUENCE: 33
000

SEQ ID NO: 34           moltype = DNA  length = 11
FEATURE                 Location/Qualifiers
misc_feature            1..11
                        note = primer
source                  1..11
                        mol_type = other DNA
                        organism = synthetic construct
SEQUENCE: 34
tgtagggaga c                                                        11

SEQ ID NO: 35           moltype = DNA  length = 13
FEATURE                 Location/Qualifiers
misc_feature            1..13
                        note = primer
source                  1..13
                        mol_type = other DNA
                        organism = synthetic construct
SEQUENCE: 35
ttgtagggag act                                                      13

SEQ ID NO: 36           moltype = DNA  length = 15
FEATURE                 Location/Qualifiers
misc_feature            1..15
                        note = primer
source                  1..15
                        mol_type = other DNA
                        organism = synthetic construct
SEQUENCE: 36
cttgtaggga gactt                                                    15

SEQ ID NO: 37           moltype = DNA  length = 11
FEATURE                 Location/Qualifiers
misc_feature            1..11
                        note = primer
source                  1..11
                        mol_type = other DNA
                        organism = synthetic construct
SEQUENCE: 37
gcgtataatg g                                                        11
```